(12) United States Patent
Smith

(10) Patent No.: US 10,792,065 B2
(45) Date of Patent: Oct. 6, 2020

(54) SURGICAL MULTI-TOOL AND METHOD OF USE

(71) Applicant: Divyze, Inc., Wellington, NV (US)

(72) Inventor: Ryan D. Smith, Wellington, NV (US)

(73) Assignee: Divyze, Inc., Wellington, NV (US)

( * ) Notice: Subject to any disclaimer, the term of this patent is extended or adjusted under 35 U.S.C. 154(b) by 0 days.

(21) Appl. No.: 15/952,572

(22) Filed: Apr. 13, 2018

(65) Prior Publication Data

US 2019/0083120 A1 Mar. 21, 2019

Related U.S. Application Data

(63) Continuation of application No. 15/628,316, filed on Jun. 20, 2017, now Pat. No. 9,943,327.
(Continued)

(51) Int. Cl.
*A61B 18/14* (2006.01)
*A61B 17/3201* (2006.01)
(Continued)

(52) U.S. Cl.
CPC ......... *A61B 17/3201* (2013.01); *A61B 17/30* (2013.01); *A61B 18/1442* (2013.01);
(Continued)

(58) Field of Classification Search
CPC ............ A61B 18/1442; A61B 18/1445; A61B 18/085; A61B 2018/1457;
(Continued)

(56) References Cited

U.S. PATENT DOCUMENTS

| 462,270 A | 11/1891 | McConnaughey |
| 2,895,478 A | 7/1959 | Post |

(Continued)

FOREIGN PATENT DOCUMENTS

| JP | 10-000199 | 1/1998 |
| JP | H10 24177 | 1/1998 |

(Continued)

OTHER PUBLICATIONS

Notice of Acceptance for AU Application No. 2014353067, dated Aug. 3, 2018.
(Continued)

*Primary Examiner* — Thomas A Giuliani
(74) *Attorney, Agent, or Firm* — Knobbe, Martens, Olson & Bear, LLP

(57) ABSTRACT

Surgical tool are disclosed that include a first tip and a second tip. The first tip and the second tip can have a first configuration, an intermediate configuration, and a second configuration. In the first configuration the tool operates as forceps and in the second configuration the tool operates as scissors. In the intermediate configuration the tool operates as a probe. The tips can be brought together to transition between the first configuration and the intermediate configuration. The tips can be rotated to transition between the intermediate configuration and the second configuration. Method are disclosed that include the step of providing a tool having a first tip extending distally and a second tip extending distally, moving at least one of the first tip and the second tip toward the other of the first tip and the second tip, and rotating the first tip and the second tip.

18 Claims, 48 Drawing Sheets

Related U.S. Application Data

(60) Provisional application No. 62/352,693, filed on Jun. 21, 2016, provisional application No. 62/437,444, filed on Dec. 21, 2016.

(51) Int. Cl.
| | |
|---|---|
| *A61B 17/30* | (2006.01) |
| *A61B 17/00* | (2006.01) |
| *A61B 17/29* | (2006.01) |
| *A61B 17/34* | (2006.01) |
| *A61B 18/00* | (2006.01) |
| *A61B 18/12* | (2006.01) |

(52) U.S. Cl.
CPC ...... *A61B 18/1445* (2013.01); *A61B 18/1206* (2013.01); *A61B 2017/00353* (2013.01); *A61B 2017/00473* (2013.01); *A61B 2017/00738* (2013.01); *A61B 2017/2923* (2013.01); *A61B 2017/305* (2013.01); *A61B 2017/3454* (2013.01); *A61B 2018/00577* (2013.01); *A61B 2018/00595* (2013.01); *A61B 2018/00601* (2013.01); *A61B 2018/1455* (2013.01); *A61B 2018/1457* (2013.01); *A61B 2018/1462* (2013.01)

(58) Field of Classification Search
CPC ...... A61B 2018/146; A61B 2018/1462; A61B 2018/00607; A61B 17/30; A61B 17/3201; A61B 2017/00353; A61B 2017/00473; A61B 2017/00738; A61B 2017/2923; A61B 2017/305; A61B 2017/3454
USPC .......................................... 606/41, 45, 50–52
See application file for complete search history.

(56) References Cited

U.S. PATENT DOCUMENTS

| | | | |
|---|---|---|---|
| 3,651,811 A | 3/1972 | Hildebrandt et al. | |
| 3,977,410 A | 8/1976 | Huston et al. | |
| 4,478,221 A | 10/1984 | Heiss | |
| 4,669,470 A | 6/1987 | Brandfield | |
| 4,819,636 A | 4/1989 | Gerich et al. | |
| 5,047,049 A | 9/1991 | Salai | |
| 5,637,111 A * | 6/1997 | Sutcu ................ | A61B 18/1445 606/174 |
| 6,096,059 A | 8/2000 | Kuzma | |
| 6,106,542 A | 8/2000 | Toybin et al. | |
| 6,283,963 B1 | 9/2001 | Regula | |
| 6,391,043 B1 | 5/2002 | Moll et al. | |
| 6,458,129 B2 | 10/2002 | Scarfi | |
| 6,592,603 B2 | 7/2003 | Lasner | |
| 6,773,434 B2 | 8/2004 | Ciarrocca | |
| 6,976,992 B2 | 12/2005 | Sachatello et al. | |
| 7,208,005 B2 | 4/2007 | Frecker et al. | |
| 7,410,494 B2 | 8/2008 | Kalmann et al. | |
| 7,544,195 B2 | 6/2009 | Lunsford et al. | |
| 8,114,074 B1 | 2/2012 | Slater | |
| 8,398,673 B2 | 3/2013 | Hinchliffe et al. | |
| 8,597,293 B2 | 12/2013 | Falkenstein et al. | |
| 9,050,101 B1 | 6/2015 | Smith | |
| 9,393,066 B2 | 7/2016 | Smith | |
| 9,931,155 B2 | 4/2018 | Smith | |
| 9,943,327 B2 * | 4/2018 | Smith ................... | A61B 17/30 |
| 2003/0065358 A1 | 4/2003 | Frecker et al. | |
| 2003/0073987 A1 | 4/2003 | Sakurai et al. | |
| 2003/0073991 A1 * | 4/2003 | Francischelli ..... | A61B 18/1442 606/41 |
| 2004/0153061 A1 | 8/2004 | Wang | |
| 2006/0167450 A1 | 7/2006 | Johnson et al. | |
| 2007/0118111 A1 * | 5/2007 | Weinberg ........... | A61B 18/1445 606/45 |
| 2007/0244515 A1 | 10/2007 | Fanous | |
| 2010/0023001 A1 | 1/2010 | Hosaka et al. | |
| 2011/0238066 A1 | 9/2011 | Olson | |
| 2012/0083827 A1 | 4/2012 | Artale et al. | |
| 2012/0209305 A1 * | 8/2012 | Deodhar .............. | A61B 17/295 606/170 |
| 2013/0178852 A1 * | 7/2013 | Allen, IV ........... | A61B 18/1442 606/42 |
| 2015/0141992 A1 * | 5/2015 | Smith ................ | A61B 18/1445 606/51 |
| 2015/0327911 A1 | 11/2015 | Smith | |
| 2017/0128125 A1 | 5/2017 | Smith | |
| 2019/0076181 A1 | 4/2019 | Smith | |

FOREIGN PATENT DOCUMENTS

| | | |
|---|---|---|
| JP | 2001037769 | 2/2001 |
| JP | 2008-100350 | 5/2008 |
| WO | WO 01/66025 | 9/2001 |
| WO | WO 2015/077350 | 5/2015 |

OTHER PUBLICATIONS

Surgical Neurology International, 2012, vol. 3, No. 152, pp. 1-3, published Dec. 14, 2012.
Written Opinion of the International Searching Authority for PCT/US2014/066432, dated Mar. 13, 2015 in 6 pages.
European Search Report for EP Application No. 14864016.2, dated Jul. 20, 2017.
Matsumura. Nobuhisa, A new bayonet spring microsurgical instrument handle 1-21 with a bar for microneurosurgery, Surgical Neurology International, 2012. vol. 3, No. 152, pp. 1-3 (internal).
Written Opinion of the International Searching Authority for PCT/US2017/038381, dated Sep. 19, 2017 in 13 pages.
Japanese Office Action for JP Application No. 2016-533089, dated Jul. 31, 2018.
First Examination Report for AU Application No. 2014353067, dated Aug. 3, 2018.

* cited by examiner

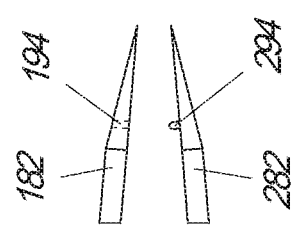

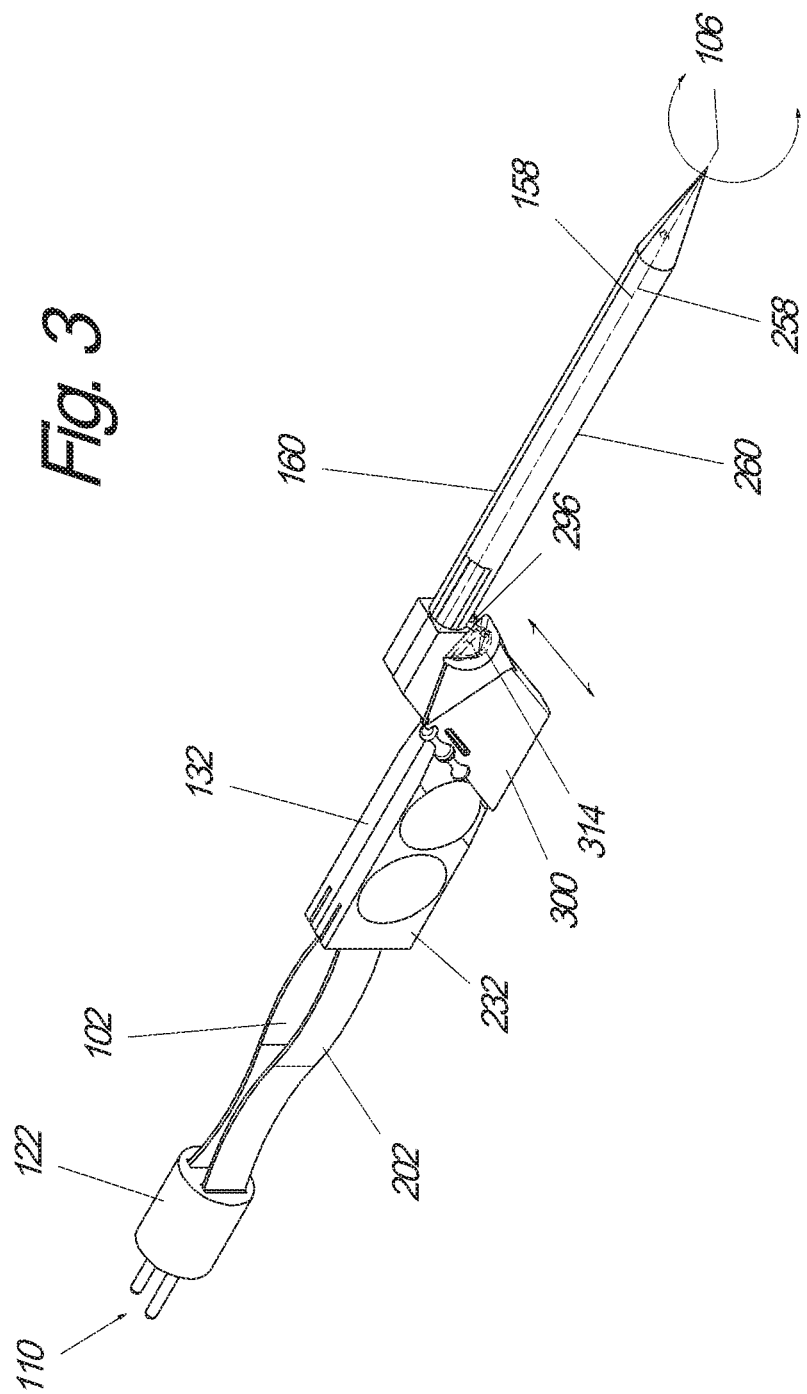

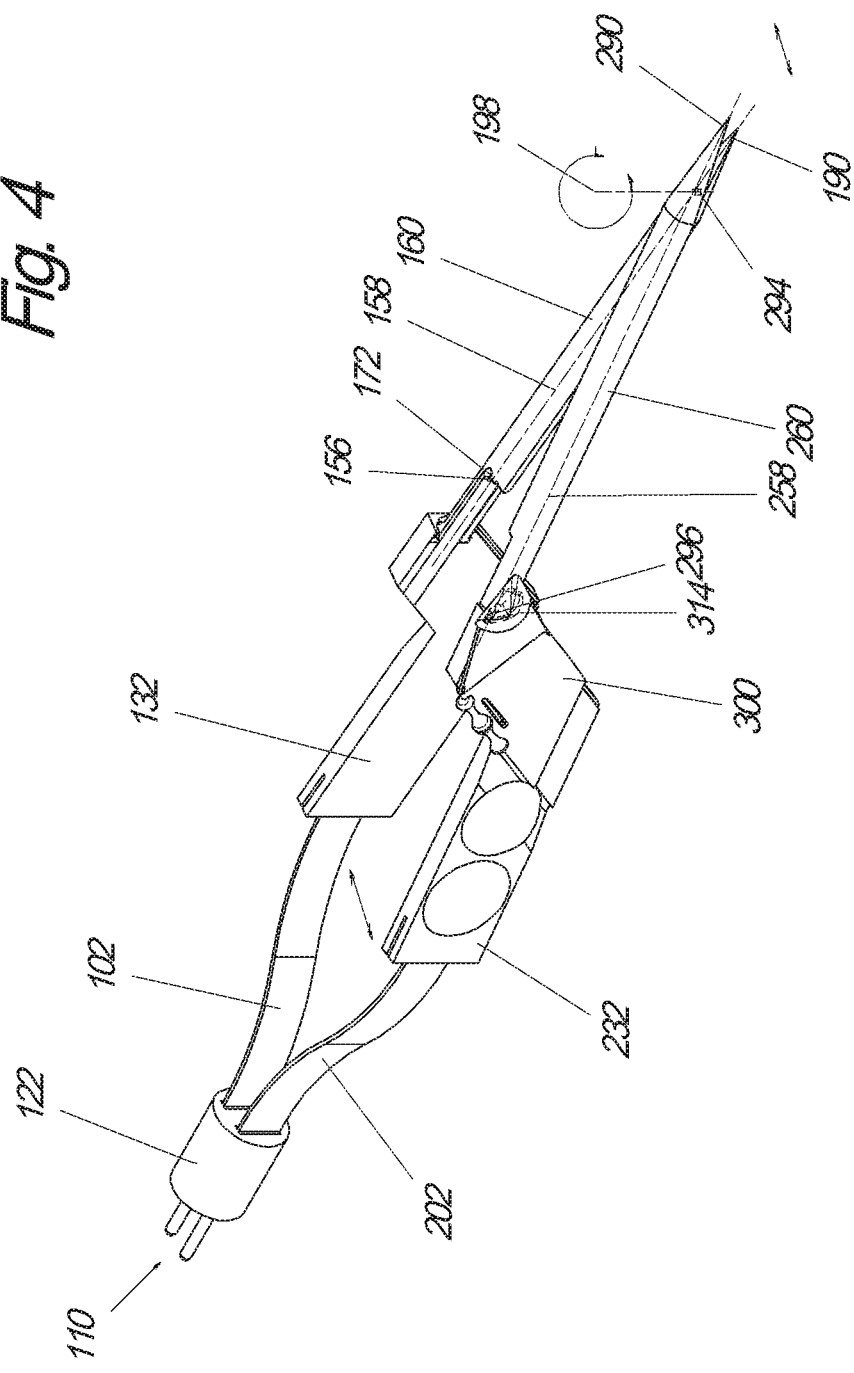

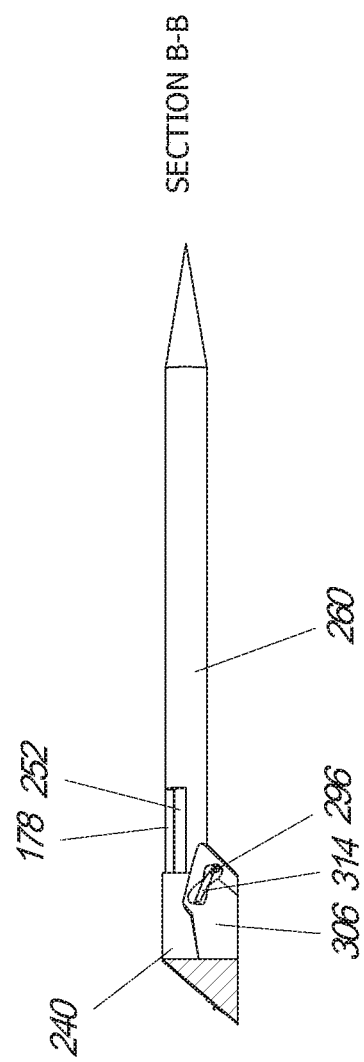

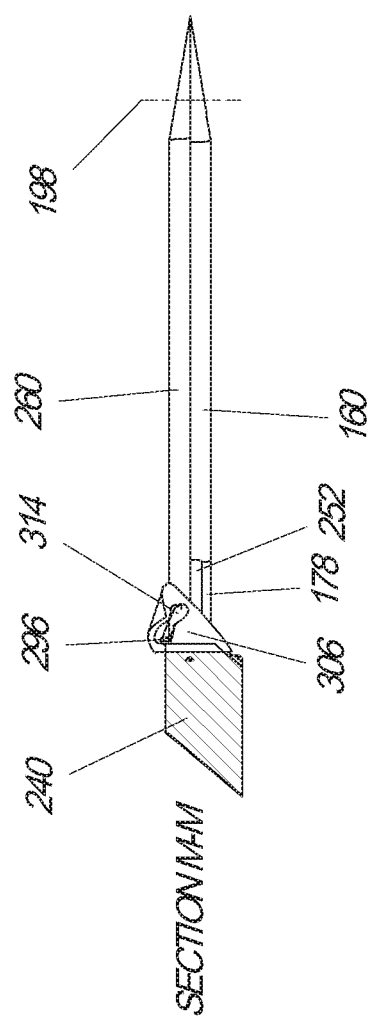

Forcep

VIEW G-G

SECTION D-D

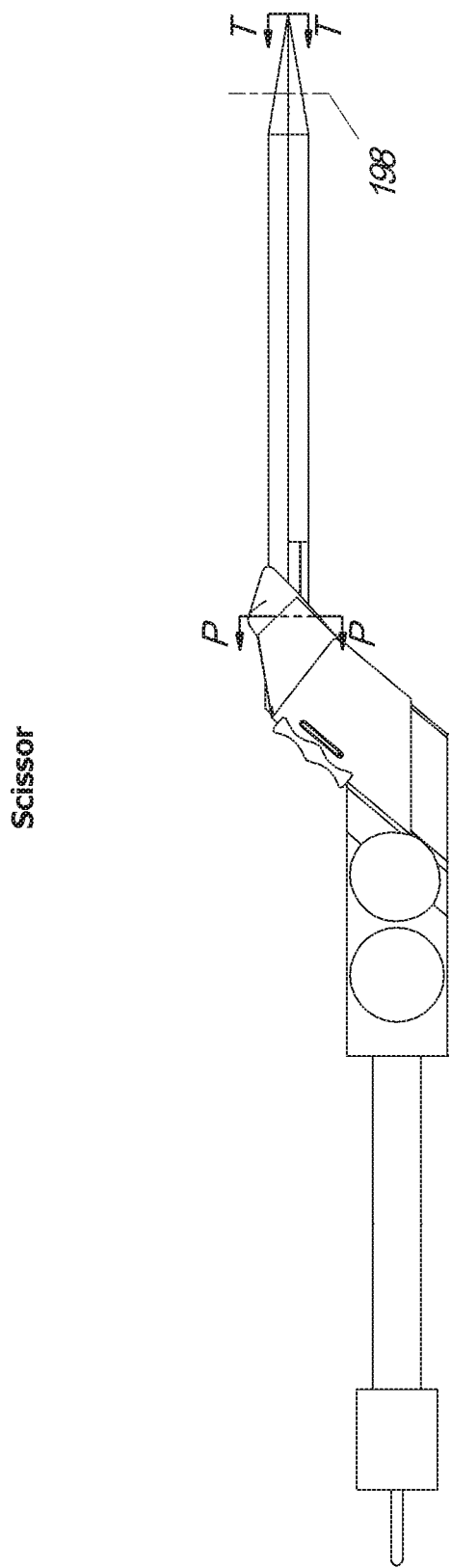

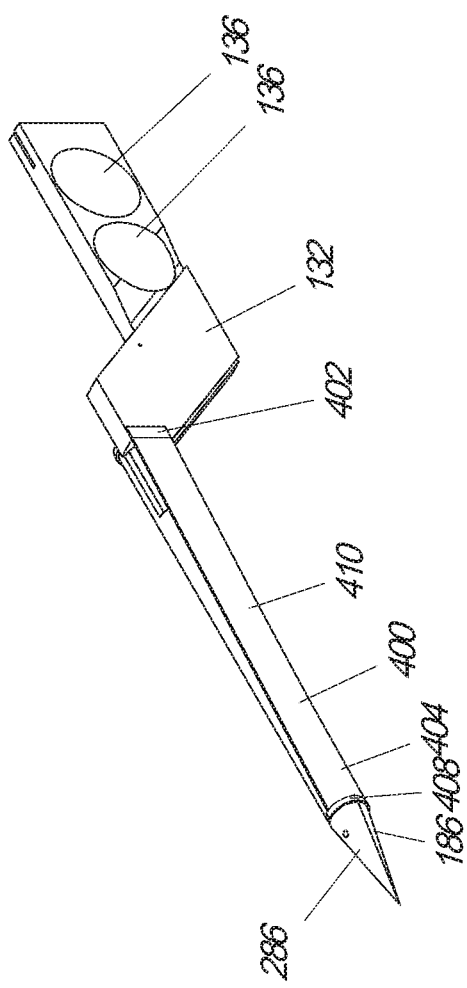

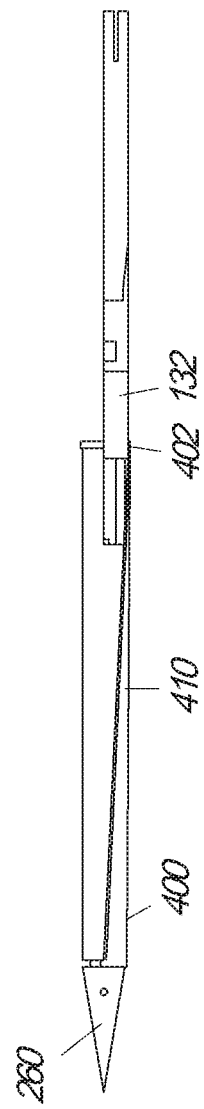

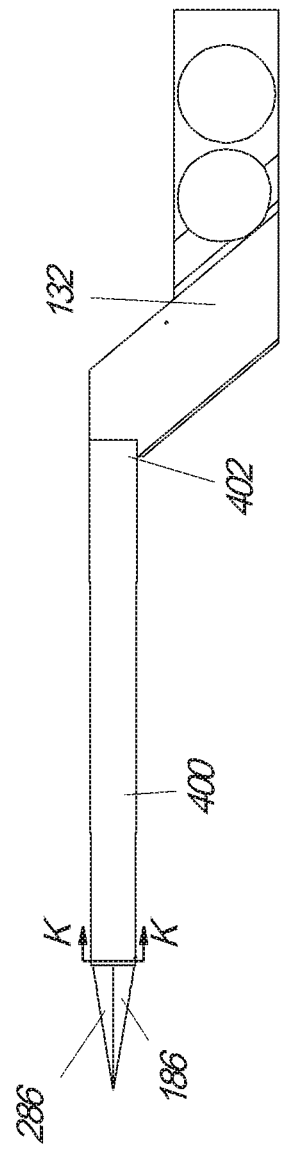

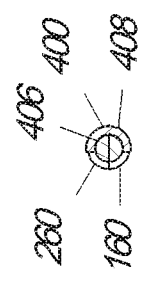

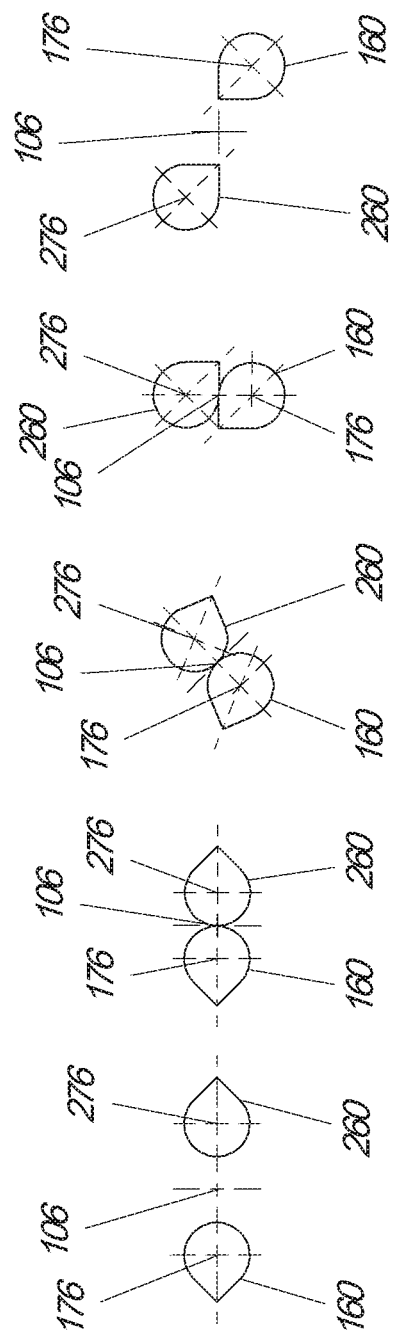

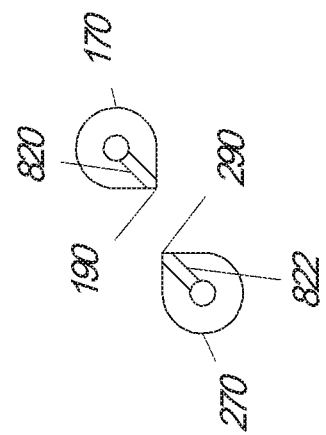
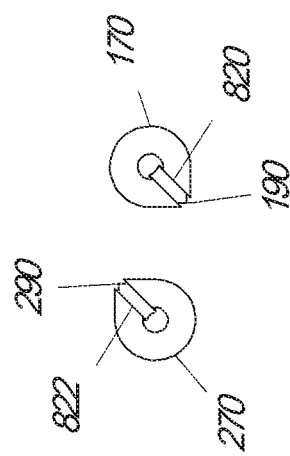

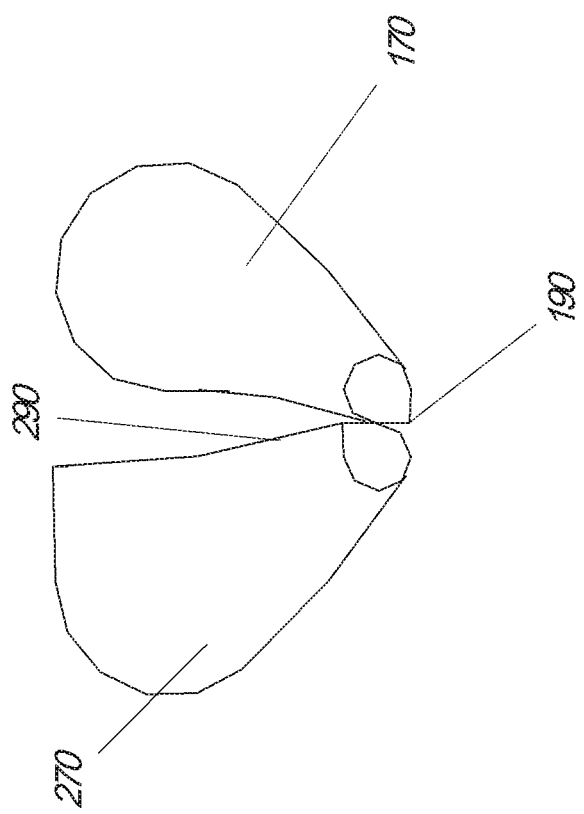

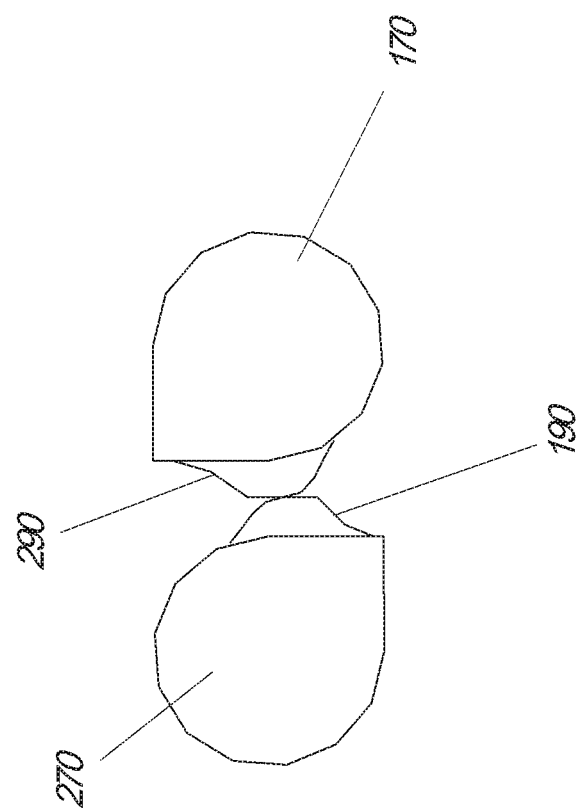

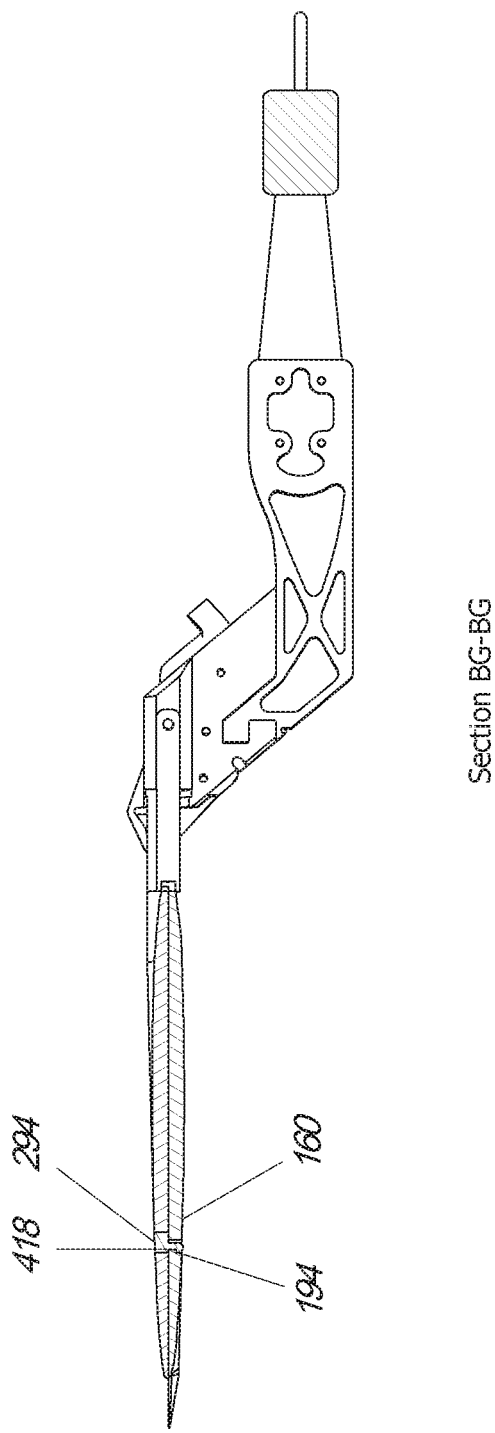

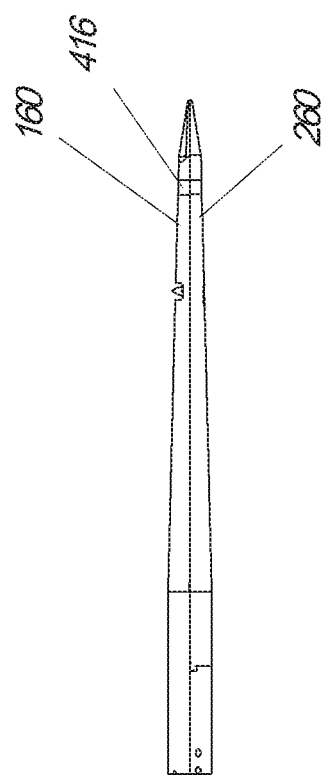

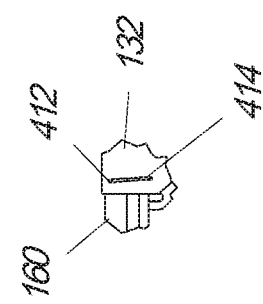

SURGICAL MULTI-TOOL AND METHOD OF USE

INCORPORATION BY REFERENCE TO ANY PRIORITY APPLICATIONS

The present application is a continuation of U.S. patent application Ser. No. 15/628,316, filed Jun. 20, 2017, now U.S. Pat. No. 9,943,327, issued Apr. 17, 2018, which claims priority benefit under 35 U.S.C. § 119(e) of U.S. Provisional Patent Application No. 62/352,693 filed Jun. 21, 2016 and U.S. Provisional Patent Application No. 62/437,444, filed Dec. 21, 2016, the disclosures of each are incorporated by reference herein in their entirety. Further details regarding apparatuses and methods that may be utilized or incorporated with the embodiments described herein are found in U.S. Pat. No. 9,050,101, issued Jun. 9, 2015 and U.S. Provisional Application No. 61/906,337 filed Nov. 19, 2013, the entireties of which are hereby incorporated by reference.

BACKGROUND OF THE INVENTION

Field of the Invention

The present application relates to the field of medical devices, and encompasses apparatuses for use during surgery and surgical methods. In particular, the application relates to surgical hand tools having a plurality of configurations including a forceps configuration, a probe configuration and a scissors configuration.

Description of the Related Art

Surgical tools typically serve a single function. Surgical scissors are useful for cutting tissue. Surgical forceps are useful for manipulating tissues. Electrosurgical devices are useful for cauterization, hemostasis, and for tissue dissection. Electrosurgical devices most commonly involve radiofrequency (RF) energy wherein a voltage gradient is produced between two points and current flows through the tissue, dissipating energy as heat. This in turn allows refolding of protein and cauterization or dissection of tissue.

Each surgical tool has limitations. For instance, in relation to electrosurgical devices, the passage of current through the tissue does not allow cutting of all tissues. This limitation is pronounced when the distance between the two contact points of the device is increased. Furthermore, tissue cutting can be accomplished more quickly with scissors in many instances where cauterization is not needed for hemostasis.

SUMMARY OF THE INVENTION

In some embodiments, a surgical tool (sometimes referred to as a hand tool) is provided. The surgical tool can include a first handle comprising a proximal portion and a distal portion and a first recess in the distal portion. The surgical tool can include a second handle comprising a proximal portion and a distal portion and a second recess in the distal portion. The surgical tool can include a first tip disposed in the first recess and extending distally therefrom, the first tip having a first external surface and a first internal surface. The surgical tool can include a second tip disposed in the second recess and extending distally therefrom, the second tip having a second external surface and a second internal surface. In some embodiments, the surgical tool has a first configuration wherein the first and second tips operate as forceps. In some embodiments, the surgical tool has a second configuration wherein the first and second tips operate as scissors. In some embodiments the surgical tool has a third configuration in which the first and second tips operate as a probe. In some embodiments, rotation of the first tip and the second tip within their respective recesses transitions the surgical tool between the first, second, and third configurations.

In some embodiments, the first inner surface and the second inner surface are configured to abut each other during rotation of the first tip and the second tip within their respective recesses to transition the surgical tool between the first configuration, the second configuration, and the third configuration. In some embodiments, the second tip comprises a pin extending from the second external surface, and rotation of the pin relative to the second handle causes rotation of the second tip relative to the second recess and transitions the surgical tool between the first configuration and the second configuration. In some embodiments, rotation of the pin relative to the second handle rotates the first tip relative to the first recess. In some embodiments, the pin is substantially perpendicular to a longitudinal axis of the second tip. In some embodiments, the first tip comprises a first electrode and the second tip comprises a second electrode. In some embodiments, the first tip and the second tip are configured to interact as electrocautery bipolar forceps in the first configuration. In some embodiments, in the second configuration, the first and second inner surfaces are configured to shear past each other. In some embodiments, one of the first tip and the second tip comprises a recess and the other of the first tip and the second tip comprises a protrusion, wherein the protrusion is configured to be received relative to the recess in the second configuration to provide an axis about which the tips can rotate. In some embodiments, the surgical tool can include a sleeve surrounding at least a portion of the first tip. In some embodiments, the surgical tool can include a locking mechanism configured to prevent rotation of the second tip. In some embodiments, the first handle is coupled to the second handle near a proximal end of the surgical tool. In some embodiments, the surgical tool can include one or more springs attached to the handles to bias the first and second tips to a neutral position.

In some embodiments, a method of using a surgical tool is provided. The method can include the step of providing a first handle and a second handle coupled to each other, the first handle having a first tip extending distally therefrom and the second handle having a second tip extending distally therefrom, wherein the first and second tips are configured for use as forceps. The method can include the step of rotating the first tip relative to the first handle and rotating the second tip relative to the second handle, wherein the rotation reconfigures the first and second tips for use as scissors. The method can include the step of rotating the first tip relative to the first handle and rotating the second tip relative to the second handle, wherein the rotation reconfigures the first and second tips for use as a probe.

The method can include the step of bringing inner surfaces of the first and second tips into proximity or contact with each other so that longitudinal axes of the first and second tips are generally aligned, and then rotating the first tip relative to the first handle and rotating the second tip relative to the second handle. In some embodiments, after rotating the first tip relative to the first handle and rotating the second tip relative to the second handle, the inner surfaces of the first and second tips are configured to shear past each other. The method can include the step of rotating a pin extending from one of the first tip and the second tip to rotate the first tip relative to the first handle and rotate the second tip relative to the second handle. The method can include the step of applying electrical energy to tissue with the first tip and the second tip. In some embodiments, rotating the first tip relative to the first handle and the second tip relative to the second handle further comprises rotating the first tip ninety degrees and rotating the second tip ninety degrees.

In some embodiments, a surgical tool is provided. The surgical tool can include a first handle. The surgical tool can include a first tip coupled to the first handle and configured to rotate relative to the first handle, the first tip having a first internal surface. The surgical tool can include a second handle. The surgical tool can include a second tip coupled to the second handle and configured to rotate relative to the second handle, the second tip having a second internal surface. In some embodiments, the surgical tool has a first configuration wherein the first internal surface and the second internal surface are generally vertical. In some embodiments, movement of the first handle or the second handle changes the distance between the first tip and the second tip in the first configuration. In some embodiments, the surgical tool has a second configuration wherein the first internal surface and the second internal surface are generally horizontal. In some embodiments, movement of the first handle or the second handle shears an edge of the first tip past an edge of the second tip in the second configuration. In some embodiments, the tips are configured to rotate to transition between the first configuration and the second configuration.

In some embodiments, a surgical tool is provided. The surgical tool can include a first handle and a second handle. In some embodiments, the first handle and the second handle are configured to have a first configuration, a second configuration, and a third configuration. In some embodiments, in the first configuration the tool operates as forceps, the second configuration the tool operates as scissors and the third configuration the tool operates as a probe.

The surgical tool or hand tool can be used in surgical sites with limited lateral access and substantial depth. The multiple configurations can allow for tissue dissection by cutting and electrocautery. The interchangeability of the hand tool limits the number of times the hand tool would need to be removed, exchanged, and re-inserted into the surgical site. The interchangeability can limit the potential for injury, while improving usability and efficiency.

The surgical tool or hand tool of certain embodiments advantageously provides multiple functional configurations that are easily interchanged by the user. The hand tool is capable of use in open microsurgery, minimally invasive surgery, and other surgical environments. The hand tool may be a single handheld device, which allows the interchangeability of configurations without the user removing the device from the local surgical field.

In some embodiments, a surgical tool is provided. The surgical tool can include a first tip and a second tip. In some embodiments, the first tip and the second tip are configured to have a first configuration, a second configuration, and a third configuration. In some embodiments, in the first configuration the tool operates as forceps and in the second configuration the tool operates as scissors. In some embodiments, in the third configuration the tool operates as a probe. In some embodiments, the tips are configured to be brought together to transition between the first configuration and the third configuration. In some embodiments, the tips are configured to be rotated to transition between the third configuration and the second configuration. In some embodiments, a method of using a surgical tool is provided.

The method can include the step of providing a tool having a first tip extending distally and a second tip extending distally. The method can include moving at least one of the first tip and the second tip toward the other of the first tip and the second tip. The method can include the step of rotating the first tip and the second tip. In some embodiments, the moving step occurs before the rotating step. In some embodiments, the probe is configured for monopolar electrocautery.

In some embodiments, a surgical tool is provided. The surgical tool can include a first tip extending distally. The surgical tool can include a second tip extending distally. In some embodiments, the surgical tool has a first configuration wherein the first and second tips operate as forceps. In some embodiments, the surgical tool has an intermediate configuration wherein the first and second tips operate as a probe. In some embodiments, the surgical tool has a second configuration wherein the first and second tips operate as scissors.

In some embodiments, bringing the first tip and the second tip together transitions the surgical tool between the first configuration and the intermediate configuration. In some embodiments, rotation of the first tip and the second tip transitions the surgical tool between the intermediate configuration and the second configuration. In some embodiments, the first tip and the second tip are configured to proximate each other in the intermediate configuration. In some embodiments, the first tip and the second tip are configured to abut each other in the intermediate configuration. In some embodiments, the first tip comprises a first electrode and the second tip comprises a second electrode. In some embodiments, the first tip and the second tip are configured to interact as electrocautery bipolar forceps in the first configuration. In some embodiments, at least one of the first tip and the second tip comprises an electrode. In some embodiments, the first tip and the second tip are configured to interact as an electrical monopolar probe in the intermediate configuration. In some embodiments, in the second configuration, the first and second tips are configured to shear past each other. In some embodiments, one of the first tip and the second tip comprises a recess and the other of the first tip and the second tip comprises a protrusion, wherein the protrusion is configured to be received relative to the recess in the second configuration to provide an axis about which the tips can rotate. In some embodiments, at least one tip is in the form of a droplet. In some embodiments, at least one tip has a retractable blade. In some embodiments, at least one tip has a foldable blade. The surgical tool can include a mechanism configured to limit the separation of the first tip and the second tip when the first tip and the second tip operate as a probe. In some embodiments, the mechanism comprises a peg and a latch. The surgical tool can include a mechanism configured to allow the surgical tool to be ambidextrous. In some embodiments, the mechanism comprises a pair of gears and a pair of cogs.

In some embodiments, a method of using a surgical tool is provided. The method can include providing a tool having a first tip extending distally and a second tip extending distally. The method can include moving at least one of the first tip and the second tip toward the other of the first tip and the second tip. The method can include rotating the first tip and the second tip.

In some embodiments, moving step occurs before the rotating step. In some embodiments, the probe is configured for monopolar electrocautery, monopolar detection, and monopolar stimulation. In some embodiments, moving further comprising bringing inner surfaces of the first and second tips into proximity with each other so that longitudinal axes of the first and second tips are generally aligned. In some embodiments, after rotating the first tip and the second tip, the inner surfaces of the first and second tips are configured to shear past each other. The method can include applying electrical energy to tissue with the first tip and the second tip. The method can include applying electrical energy to tissue with only one of the first tip and the second tip. In some embodiments, rotating the first tip and the second tip further comprises rotating the first tip ninety degrees and rotating the second tip ninety degrees.

In some embodiments, a surgical tool is provided. The surgical tool can include a first tip extending distally. The surgical tool can include a second tip extending distally. In some embodiments, the surgical tool has a first configuration wherein the first and second tips operate as forceps. In some embodiments, the surgical tool has a second configuration wherein the first and second tips operate as scissors. In some embodiments, the surgical tool has a third configuration wherein the first and second tips operate as a probe.

In some embodiments, the third configuration is an intermediate configuration between the first configuration and the second configuration. In some embodiments, bringing the first tip and the second tip together allows transition of the surgical tool between the first configuration and the third configuration. In some embodiments, rotation of the first tip and the second tip transitions the surgical tool between the third configuration and the second configuration. In some embodiments, the first tip and the second tip are configured to proximate each other in the third configuration. In some embodiments, the first tip and the second tip are configured to abut each other in the third configuration. In some embodiments, the first tip comprises a first electrode and the second tip comprises a second electrode. In some embodiments, the first tip and the second tip are configured to interact as electrocautery bipolar forceps in the first configuration. In some embodiments, at least one of the first tip and the second tip comprises an electrode. In some embodiments, the first tip and the second tip are configured to interact as an electrical monopolar probe in the third configuration. In some embodiments, at least one of the first tip and the second tip comprises a plurality of electrodes. In some embodiments, the first tip and the second tip are configured to interact as electrical conductors. In some embodiments, in the second configuration, the first and second tips are configured to shear past each other. In some embodiments, one of the first tip and the second tip comprises a recess and the other of the first tip and the second tip comprises a protrusion, wherein the protrusion is configured to be received relative to the recess in the second configuration to provide an axis about which the tips can rotate. In some embodiments, at least one tip is in the form of a droplet. In some embodiments, at least one tip has a retractable blade. In some embodiments, at least one tip has a foldable blade. In some embodiments, the surgical tool can include a mechanism configured to limit the separation of the first tip and the second tip. In some embodiments, the mechanism comprises a peg and a latch. In some embodiments, the surgical tool can include a mechanism configured to allow the surgical tool to be ambidextrous. In some embodiments, the mechanism comprises a pair of gears and a pair of cogs.

In some embodiments, a method of using a surgical tool is provided. The method can include providing a tool having a first tip extending distally and a second tip extending distally. The method can include moving at least one of the first tip and the second tip toward the other of the first tip and the second tip, wherein the moving allows for reconfiguration of the tool for use as a probe. The method can include rotating the first tip and the second tip, wherein the rotating reconfigures the tool for use as scissors.

In some embodiments, the moving step occurs before the rotating step. In some embodiments, when configured for use as a probe, the tool is configured for monopolar electrocautery, monopolar detection, or monopolar stimulation. In some embodiments, when configured for use as a probe, the tool is configured for multipolar electrocautery, multipolar detection, or multipolar stimulation. In some embodiments, moving further comprises bringing inner surfaces of the first and second tips into proximity with each other so that longitudinal axes of the first and second tips are generally aligned. In some embodiments, after rotating the first tip and the second tip, the inner surfaces of the first and second tips are configured to shear past each other. In some embodiments, the method can include applying electrical energy to tissue with the first tip and the second tip. In some embodiments, the method can include applying electrical energy to tissue with only one of the first tip and the second tip. In some embodiments, wherein rotating the first tip and the second tip further comprises rotating the first tip ninety degrees and rotating the second tip ninety degrees.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 2B is a top view of the hand tool of FIG. 1 in the forceps configuration.

FIG. 3 is a perspective view of the hand tool of FIG. 1, wherein the tips are brought together to change configurations.

FIG. 4 is a perspective view of the hand tool of FIG. 1 in the scissors configuration.

FIG. 5B is a cross-sectional view taken along line B-B in FIG. 5A.

FIG. 6B is a cross-sectional view taken along line M-M in FIG. 6A.

FIG. 8A is a side view of the hand tool of FIG. 1 in the scissors configuration.

FIG. 9A is a perspective view of a hand tool in the scissors configuration with a sleeve; FIG. 9B is a top view of the hand tool of FIG. 9A; FIG. 9C is side view of the hand tool of FIG. 9A; and FIG. 9D is a cross-sectional view taken along line K-K in FIG. 9A.

FIGS. 11A-11E show one illustration of the movement of the tips.

FIGS. 12A-15 show embodiments of the tips.

FIGS. 16-26 show view of an embodiment of the hand tool.

FIGS. 31-32B show embodiments of a hand tool.

FIG. 33 shows an embodiment of a guiding slot in a handle.

DETAILED DESCRIPTION OF THE PREFERRED EMBODIMENTS

Preferred embodiments of the surgical hand tool include two sections used together to perform a function. One or more of the sections can comprise segments, portions, components, or subcomponents. However, the use of the term "section" does not imply any particular structure or configuration. In some embodiments, the right section or components thereof are mirror image, identical, or substantially similar to the left section or components thereof. The sections or components thereof may be any suitable shape that permits the function of the hand tool, for instance perform the function of scissors, forceps, and probe. Certain embodiments are illustrated and/or described herein.

Figure 1:
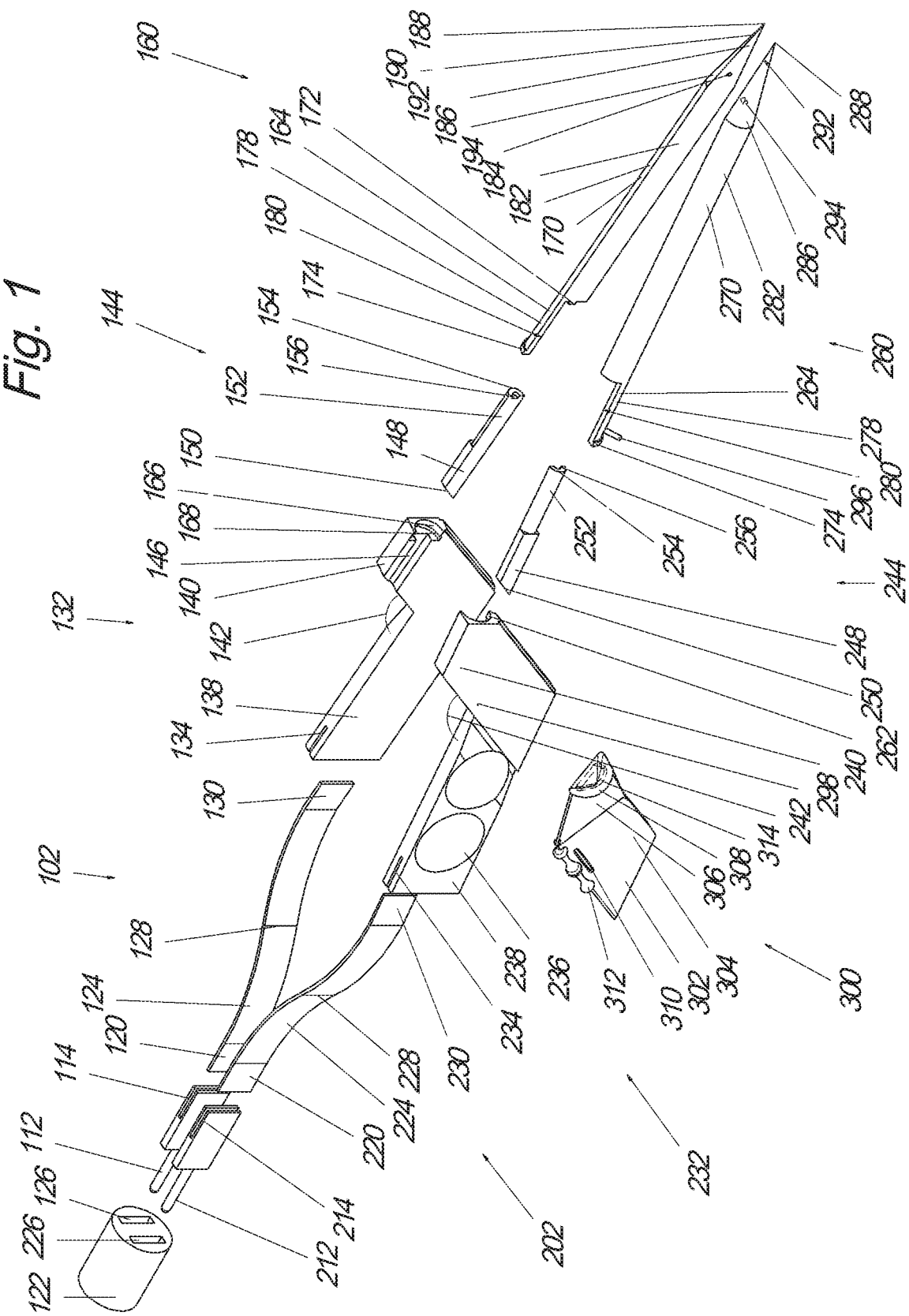
FIG. 1 is an exploded view of a hand tool.
Figure 2A:
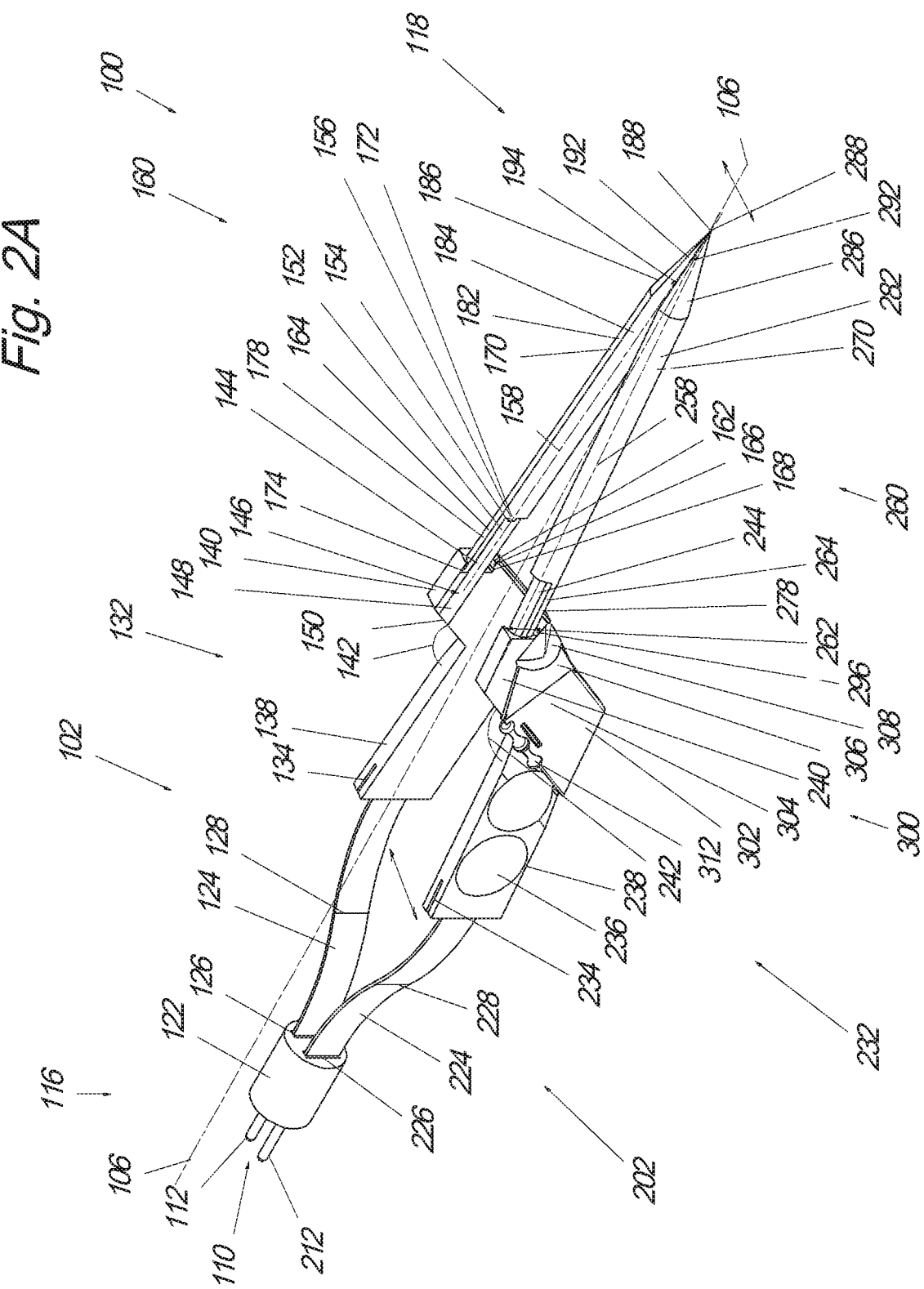
FIG. 2A is a perspective view of the hand tool of FIG. 1 in the forceps configuration.

With reference to FIGS. 1-2A, a hand tool 100 is shown. The hand tool 100 can also be referred to as a surgical multi-tool. The hand tool 100 comprises two sections: a left section 102 and a right section 202. In the illustrated configuration, the left section 102 includes multiple components and the right section 202 includes multiple components as described further below. The left section 102 interacts with the right section 202 to perform one or more functions, such as operating as forceps, scissors, and probe as described in detail below. The hand tool 100 has a longitudinal axis 106 that extends between a proximal end 116 and a distal end 118. The left section 102 can be on the left side of the longitudinal axis 106 when the hand tool 100 is viewed from the top. The right section 202 can be on the right side of the longitudinal axis 106 when the hand tool 100 is viewed from the top.

The surgical hand tool 100 can transition between functional configurations. As illustrated in FIGS. 1 and 2A, the left section 102 can comprise a left handle 132 and a left tip 160 extending distally from the left handle 132. The right section 202 can comprise a right handle 232 and a right tip 260 extending distally from the right handle 232. The surgical hand tool can operate as forceps, which can also be referred to as the forceps configuration, with the left tip 160 and the right tip 260 providing the grasping ends of the forceps. In this and other configurations, the surgical hand tool 100 can also include electrodes. For example, the surgical hand tool of FIGS. 1 and 2A can function as electrocautery bipolar forceps, as described further below. The surgical hand tool can further be configured to operate as scissors, which can also be referred to as the scissors configuration. FIG. 4, described in more detail below, illustrates a scissors configuration where the tips 160, 260 slide and pivot relative to each other to cut tissue. The scissors can be utilized to more quickly cut tissue. The surgical hand tool can further be configured to operate as a probe, which can also be referred to as the probe configuration. The multiple configurations allow for the use of multiple surgical techniques at the discretion of the user. Other functional configurations are possible.

Referring now to FIGS. 2A-4, the hand tool 100 is designed to transition between the forceps configuration and the scissors configuration. The forceps configuration is shown in FIG. 2A and the scissors configuration is shown in FIG. 4. The intermediate configuration is shown in FIG. 3. The hand tool 100 permits the switching between the forceps configuration and the scissors configuration. The hand tool 100 can transition between these configurations by rotation of the tips 160, 260 of the hand tool 100, as described further below. The tips 160, 260 are rotated approximately 90 degrees between the forceps configuration shown in FIG. 2A and the scissors configuration shown in FIG. 4. The tips can be brought together as shown in FIG. 3 during the transition between the forceps configuration and the scissors configuration.

Components of the Hand Tool

In some embodiments, the forceps configuration as shown in FIG. 2A can operate as bipolar electrocautery forceps. For instance, the hand tool 100 can include one or more electrodes located on the tips of the hand tool. The hand tool 100 can be designed to supply electrical energy to the electrodes. In some embodiments, the hand tool 100 can optionally include an electrical connection 110. The electrical connection 110 can include a left lead 112 and a right lead 212. The electrical connection 110 can enable the electrodes to be supplied with electrical energy. In the illustrated configuration, the electrical connection 110 can be near the proximal end 116 of the hand tool 100.

In some embodiments, the hand tool 100 can include a mechanical connector 122. The mechanical connector 122 can function to electrically isolate the incoming electrical leads 112, 212. The mechanical connector 122 can function to couple the left section 102 and the right section 202.

The left lead 112 can include a receptacle 114. The receptacle 114 can be sized to accept the left spring 124. The left section 102 can include a left spring 124 that extends along the longitudinal axis 106. The left spring 124 can be coupled to the mechanical connector 122. In some embodiments, the left spring 124 can have an external shape that complements the shape of a receptacle 126 in the mechanical connector 122. In the illustrated embodiment, the shape of the left spring 124 is rectangular and the shape of the receptacles 126 is rectangular. Other shapes are contemplated (e.g., wedge, oval, triangular, elliptical, polygonal, etc.). The left spring 124 can be coupled to the mechanical connector 122 by welding, fasteners, glue, friction fit, pawl and ratchet, detent and protrusion, or other fixation method. The left spring 124 can be coupled to the left lead 112 of the electrical connection 110. In the illustrated embodiment, the left spring 124 is coupled to the left lead 112 within the mechanical connector 122. The left spring 124 can be coupled to the left lead 112 by welding, fasteners or other fixation method.

The left spring 124 can include a bend 128. The bend 128 can function to extend the distal end of the left spring 124 away from the longitudinal axis 106. The bend 128 can function to curve the left spring 124 outward from the mechanical connector 122. The bend 128 of the left spring 124 can function to increase the distance between the left section 102 and the right section 202. The left spring 124 can include a concave portion. The concave portion can be near the proximal end of the left spring 124. The left spring 124 can include a convex portion. In the illustrated embodiment, the convex portion can be near the distal end of the left spring 124. The left spring 124 can include one or more flat portions 120, 130. In the illustrated embodiment, the flat portion 120 can be disposed within the receptacle 114. In other configurations the flat portion can be near the proximal end, distal end, or in between the proximal and distal end of the left spring 124. Other configuration of the spring can be contemplated (e.g., multiple bends, flat portions, multiple layers, thicknesses, varying thickness, height and length, etc.).

The distal end of the left spring 124 can be coupled to a left handle 132. In some embodiments, the left spring 124 can have an external shape that complements the shape of a receptacle 134 in the left handle 132. In the illustrated embodiment, the flat portion 130 can be disposed within the receptacle 134. In the illustrated embodiment, the shape of the left spring 124 is rectangular and the shape of the receptacle 134 is rectangular. Other configurations are contemplated (e.g., wedge, oval, triangular, elliptical, polygonal, etc.). The left spring 124 can be coupled to the left handle 132 by welding, fasteners, glue, friction fit, pawl and ratchet, detent and protrusion, or other fixation method. In the illustrated embodiment, the receptacle 134 is a slot that extends from the top of the left handle 132 to the bottom of the left handle 132, or a portion thereof. In some embodiments, the left spring 124 can be adjustable within the receptacle 134 of the left handle 132. In some embodiments, the left spring 124 can be adjusted to a number of discrete positions with the receptacle 134 (e.g., two, three, four, five, etc.). In some embodiments, the left spring 124 can be adjusted to an infinite number of positions with the receptacle 134. The left spring 124 can remain movable, releasably retained or fixedly retained in position.

The left handle 132 can include one or more finger grips 136 (see FIG. 9A). In the illustrated embodiment, two finger grips 136 are shown. Other numbers of finger grips are contemplated (e.g., one, two, three, four, five, etc.). Both of the finger grips 136 are shown on the exterior surface of the left handle 132. Other locations are possible (e.g., top surface, bottom surface, interior surface, at least one grip on the exterior surface, at least one grip on the top surface, a grip on the top surface and a grip on the exterior surface, etc.).

The left handle 132 can have a bayonet configuration. The left handle 132 can include a longitudinally extending portion 138 and a vertically extending portion 140. The longitudinally extending portion 138 can extend generally along the longitudinal axis 106. The vertically extending portion 140 can extend upward from the longitudinally extending portion 138. The vertically extending portion 140 can improve the line of sight for the user. The user's hand can engage the longitudinally extending portion 138. The vertically extending portion 140 can raise the distal end 118 of the hand tool 100 away from the user's hand. The user's hand does not obstruct the line of sight to the distal end 118 of the hand tool 100. In the illustrated embodiment, the vertically extending portion 140 forms an angle 142 with the longitudinally extending portion 138. The angle 142 can be 90° or greater than 90° (e.g., 100°, 110°, 120°, 130°, 140°, 150°, 160°, 170°, etc.). The angle 142 can be obtuse. Other configurations are possible. The angle 142 can provide a more ergonomic grip to the user.

The left section 102 can include a left hub 144. The left hub 144 can extend from the vertically extending portion 140. In some embodiments, the left hub 144 can be a unitary structure with the vertically extending portion 140 of the left handle 132. The left hub 144 and the left handle 132 can be monolithically formed.

In other embodiments, the left hub 144 is a separate component from the left handle 132. The vertically extending portion 140 can include a recess 146. The left hub 144 can be coupled to the recess 146 by welding, fasteners, glue, friction fit, pawl and ratchet, detent and protrusion, or other fixation method. In some embodiments, the left hub 144 is removable from the vertically extending portion 140. For instance, the left hub 144 can be removed to permit sterilization of the left tip 160. The left hub 144 can be removed to replace the left tip 160.

The left hub 144 can include a proximal portion 148. The proximal portion 148 of the left hub 144 can be received within the recess 146 of the vertically extending portion 140. The recess 146 can be shaped to complement the external surface of the proximal portion 148. The proximal portion 148 can be any cross-sectional shape including semi-circular, triangular, rectangular, etc. In some embodiments, the proximal portion 148 can extend the entire length of the vertically extending portion 140. The edge 150 of the proximal portion 148 can be angled to match the angle 142.

The left hub 144 can include a distal portion 152. The distal portion 152 can extend from the vertically extending portion 140. The distal portion 152 can extend from the recess 162 when proximal portion 148 is received within the recess 162. The edge 154 of the distal portion 152 can include a hub recess 156. The distal portion 152 can be a portion of a cylinder. The distal portion 152 can be any cross-sectional shape including semi-circular. In some embodiments, the proximal portion 148 and the distal portion 152 have the same cross-sectional shape. In other embodiments, the proximal portion 148 and the distal portion 152 have different cross-sectional shapes. In some embodiments, the proximal portion 148 and the distal portion 152 can have the same diameter. In other embodiments, the proximal portion 148 and the distal portion 152 have different diameters.

The left hub 144 can define a left tip axis 158. The left tip axis 158 can be the axis upon which the left tip 160 rotates. The distal portion 152 of the left hub 144 can function to support the left tip 160 during rotation. The hub recess 156 can be aligned with the left tip axis 158. The hub recess 156 can function to maintain alignment of the left tip 160 during rotation. In some methods of assembly, the left hub 144 is coupled to the vertically extending portion 140. This can create a channel between the external surface of the left hub 144 and the internal surface of the recess 162. A portion of the left tip 160 can rotate within this channel.

The left tip 160 can include a proximal portion 164. The proximal portion 164 of the left tip 160 can be supported by the left hub 144. The proximal portion 164 of the left tip 160 can rotate about the left hub 144. At least a portion of the proximal portion 164 of the left tip 160 can be received within the recess 162 of the vertically extending portion 140.

In the illustrated embodiment, the recess 162 of the vertically extending portion 140 can include a first portion 166 and a second portion 168. The first portion 166 can have a circular cross-section and the second portion 168 can have a circular cross-section. The first portion 166 can have a semi-circular cross-section and the second portion 168 can have a semi-circular cross-section. The cross-sectional shapes of the first portion 166 and the second portion 168 can permit rotation of the left tip 160 within the recess 162.

The first portion 166 can have a first diameter and the second portion 168 can have a second diameter. The first diameter can be smaller than the second diameter. The first portion 166 can be located distal to the second portion 168. The first portion 166 of the recess 162 can be closer to the distal end 118. The second portion 168 can be located proximal to the first portion 166. The second portion 168 of the recess 162 can be closer to the proximal end 116. The difference in diameter between the first portion 166 and the second portion 168 of the recess 162 can create a lip.

The recess 162 can have any number of portions (e.g., two, three, four, five, six, etc.). Each portion can have a diameter that is either the same or different than one or more other portions. At least two of the portions have unequal diameters. Of the at least two portions, a portion near the distal end can have a smaller diameter than another portion near the proximal end. The difference in diameter between the portions of the recess 162 can create a lip.

In the illustrated embodiment, the left tip 160 can include a ridge 174 which can interact with the lip. The ridge 174 can extend from the external surface of the proximal portion 164 of the left tip 160. The ridge 174 can be sized to be received within the second portion 168 of the recess 162. For instance, the ridge 174 and the second portion 168 can have the same or similar diameter. The ridge 174 can have a larger diameter than the first portion 166. The ridge 174 can abut the lip created by the first portion 166 and the second portion 168. The ridge 174 can define axial translation of the left tip 160 when the left tip 160 is received within the recess 162. The ridge 174 can reduce the longitudinal movement of the left tip 160 when the ridge 174 is received within the recess 162. The ridge 174 can prevent disengagement between the vertically extending portion 140 and the left tip 160 by the application of axial force. Any shape can be used to define or limit axial translation (ridge, pin, etc.).

The proximal portion 164 of left tip 160 can include a left extension 178 which can interact with the hub 144. The left extension 178 can be a portion of a cylinder. In some embodiments, the left extension 178 can have a quarter-circular cross-section (e.g., encompasses 90 degrees). The left extension 178 can have a convex external surface. The convex external surface can be complementary to the second portion 168. The left extension 178 can have a concave internal surface 180. The concave internal surface 180 can be complementary to the external surface of the distal portion 152 of the left hub 144.

The proximal portion 164 of left tip 160 can include a protrusion 172 which can interact with the hub recess 156. The protrusion 172 is sized to be received within the hub recess 156. For instance, the protrusion 172 and the hub recess 156 can have the same or similar diameter. The protrusion 172 can extend along the left tip axis 158 when the ridge 174 is received within the recess 162. The protrusion 172 and the hub recess 156 can provide a pivot for the left tip 160 as the left tip 160 rotates.

The left tip 160 can include a distal portion 170. The distal portion 170 of the left tip 160 can include a longitudinally extending portion 182. The longitudinally extending portion 182 can be a portion of a cylinder. In some embodiments, the longitudinally extending portion 182 can have a semi-circular cross-section (e.g., encompasses 180 degrees). The longitudinally extending portion 182 can have a convex external surface. The distal 170 and longitudinally extending 182 portions can have other cross-sectional shapes (e.g., circular, elliptical, square, rectangular, triangular, polygonal, sigmoid, etc.).

The distal portion 170 of the left tip 160 can include a conical portion 186. The conical portion 186 can extend to a distal tip 188. The conical portion 186 and distal tip 188 can interact with the right section 202 to function as forceps. The conical portion 186 can include a cutting edge 190. The cutting edge 190 can interact with the right section 202 to function as scissors. The cutting edge 190 can be the same material as the distal portion 170 of the left tip 160. The cutting edge 190 can be the same material as the left tip 160. The cutting edge 190 can be a different material than the distal portion 170 of the left tip 160. The cutting edge 190 can be a different material than the left tip 160. The cutting edge 190 can be integrally or monolithically formed with the left tip 160. The cutting edge 190 can be a separate component and coupled to the left tip 160.

The distal portion 170 of the left tip 160 can have a flat internal surface 184. The flat internal surface 184 can be complementary to an internal surface of the right section 202. The flat internal surface 184 can extend the length of the longitudinally extending portion 182. The flat internal surface 184 can extend the length of the conical portion 186. The flat internal surface 184 can abut a flat internal surface of the right tip. Other cross-sectional shapes of the internal surface can be contemplated (e.g., circular, elliptical, square, rectangular, triangular, polygonal, sigmoid etc.). These can be complimentary, mirror or rotationally similar to the right tip 260.

The distal portion 170 of the left tip 160 can include an electrode 192. In some embodiments, the longitudinally extending portion 182 can include the electrode 192. In some embodiments, the conical portion 186 can include the electrode 192. In some embodiments, the distal tip 188 can include the electrode 192. In some embodiments, the flat internal surface 184 can include the electrode 192. In some embodiments, the external surface of the left tip 160 can include the electrode 192. The electrode 192 can interact with the right section 202. The right section 202 can include a ground or another electrode. The left tip 160 can interact with the right section to function as an electrosurgical device. The electrode 192 can be activated by electrical energy supplied to the hand tool 100. The electrode 192 can be activated when the hand tool 100 is in the forceps configuration. In some embodiments, electrical energy is prevented from being supplied when the hand tool 100 is in the scissors configuration. The electrode 192 can be the same material as the distal portion 170 of the left tip 160. The electrode 192 can be the same material as the left tip 160. The electrode 192 can be a different material than the distal portion 170 of the left tip 160. The electrode 192 can be a different material than the left tip 160. The electrode 192 can be integrally or monolithically formed with the left tip 160. The electrode 192 can be a separate component and coupled to the left tip 160.

In some embodiments, the left lead 112 can pass through a channel in the left spring 124. The left lead 112 can pass through a channel in the left handle 132. The left lead 112 can pass through a channel in the left tip 160. The channels in any of the components in the left section 102 can be insulated.

In some methods of assembly, the left tip 160 is inserted within the recess 162. Then the left hub 144 is coupled to the vertically extending portion 140. The left tip 160 is place in the recess prior to coupling of the left hub 144. The left tip 160 can be retained within the recess 162 by a retention mechanism (not shown). In some embodiments, the left hub 144 is removable. The left hub 144 can be removed to replace the left tip 160. The left hub 144 can be removed to sterilize or replace the left tip 160.

In some embodiments, the left hub 144 is integrally formed with the vertically extending portion 140. Then the left tip 160 is inserted within the recess 162. The ridge 174 is aligned with the second portion 168 the recess 162 in the vertically extending portion 140. The internal surface 180 of the left extension 178 is aligned with the external surface of the left hub 144. The protrusion 172 of the left tip 160 is aligned with the hub recess 146. From this position, the left tip 160 can be rotated about the left tip axis 158. The left tip 160 can be rotated until the ridge 174 is received within the second portion 168 of the recess 162. In this position, the internal surface 180 of the left extension 178 can be in contact with the external surface of the left hub 144. In this position, protrusion 172 can be received within the hub recess 146.

In some embodiments, the left section 102 and the right section 202 each form of a symmetrical, opposed half. The right section 202 can be a mirror image of the left section 102. The right section 202 can include substantially similar or identical components. In some embodiments, the right section 202 may have a different shape or configuration to enhance ergonomics for the user.

The right lead 212 can include a receptacle 214. The receptacle 214 can be sized to accept the right spring 224. The right section 202 can include a right spring 224 that extends along the longitudinal axis 106. The right spring 224 can be coupled to the mechanical connector 122. In some embodiments, the right spring 224 can have an external shape that complements the shape of a receptacle 226 in the mechanical connector 122. In the illustrated embodiment, the shape of the right spring 224 is rectangular and the shape of the receptacles 226 is rectangular. Other configurations are contemplated (e.g., wedge, oval, triangular, elliptical, polygonal, etc.). The right spring 224 can be coupled to the mechanical connector 122 by welding, fasteners, glue, friction fit, pawl and ratchet, detent and protrusion, or other fixation method. The right spring 224 can be coupled to the right lead 212 of the electrical connection 110. In the illustrated embodiment, the right spring 224 is coupled to the right lead 212 within the mechanical connector 122. The right spring 224 can be coupled to the right lead 212 by welding, fasteners or other fixation method.

The right spring 224 can include a bend 228. The bend 228 can function to extend the distal end of the right spring 224 away from the longitudinal axis 106. The bend 228 can function to curve the right spring 224 outward from the mechanical connector 122. The bend 228 of the right spring 224 can function to increase the distance between the left section 102 and the right section 202. The right spring 224 can include a concave portion. The concave portion can be near the proximal end of the right spring 224. The right spring 224 can include a convex portion. In the illustrated embodiment, the convex portion can be near the distal end of the right spring 224. The right spring 224 can include one or more flat portions 220, 230. In the illustrated embodiment the flat portion 220 can be disposed within the receptacle 214. In other configurations the flat portion can be near the proximal end, distal end, or in between the proximal and distal end of the right spring 224. The right spring 224 can provide the same or different resistance as the left spring 124. The right spring 224 can provide the same or different shape as the left spring 124. The right spring 224 can be a mirror image of the left spring 124.

The distal end of the right spring 224 can be coupled to a right handle 232. In some embodiments, the right spring 224 can have an external shape that complements the shape of a receptacle 234 in the right handle 232. In the illustrated embodiment the flat portion 230 can be disposed within the receptacle 234. In the illustrated embodiment, the shape of the right spring 224 is rectangular and the shape of the receptacle 234 is rectangular. Other configurations are contemplated (e.g., wedge, oval, triangular, elliptical, polygonal, etc.). In the illustrated embodiment, the receptacle 234 is a slot that extends from the top of the right handle 232 to the bottom of the right handle 232, or a portion thereof. In some embodiments, the right spring 224 is coupled to the right handle 232 by welding, fasteners, glue, friction fit, pawl and ratchet, detent and protrusion, or other fixation method. In some embodiments, the right spring 224 is adjustable within the receptacle 234 of the right handle 232. In some embodiments, the right spring 224 can be adjusted to a number of discrete positions with the receptacle 234 (e.g., two, three, four, five, etc.). In some embodiments, the right spring 224 can be adjusted to an infinite number of positions with the receptacle 234. The right spring 224 can remain movable, releasably retained or fixedly retained in position. In some embodiments, the right spring 224 is movable and the left spring 124 is fixed. At least one spring 124, 224 can be movable to accommodate the user's hand. In some embodiments, both springs 124, 224 are movable to accommodate the user's hand.

The right handle 232 can include one or more finger grips 236. In the illustrated embodiment, two finger grips 236 are shown but other configurations are contemplated (e.g., one, two, three, four, five, etc.). Both of the finger grips 236 are shown on the exterior surface of the right handle 232. Other locations are possible (e.g., top surface, bottom surface, interior surface, at least one grip on the exterior surface, at least one grip on the top surface, a grip on the top surface and a grip on the exterior surface, etc.). The finger grips 236 can have the same or different configuration as the finger grips 136. For instance, one set of finger grips can be shaped for the index finger and the other set of grips can be shaped for the thumb. The finger grips 136, 236 can be positioned based on the manner in which the user is expected to hold the hand tool 100. The finger grips 136, 236 can be positioned based on right handed use. The finger grips 136, 236 can be positioned based on left handed use. The finger grips 136, 236 can be positioned based on ambidextrous use.

The right handle 232 can have a bayonet configuration. The right handle 232 can include a longitudinally extending portion 238 and a vertically extending portion 240. The longitudinally extending portion 238 can extend generally along the longitudinal axis 106. The vertically extending portion 240 can extend upward from the longitudinally extending portion 238. The vertically extending portion 240 can improve the line of sight for the user. The user's hand can engage the longitudinally extending portion 238. The vertically extending portion 240 can raise the distal end 118 of the hand tool 100 away from the user's hand. The user's hand does not obstruct the line of sight to the distal end 118 of the hand tool 100. In the illustrated embodiment, the vertically extending portion 240 forms an angle 242 with the longitudinally extending portion 238. The angle 242 can be 90° or greater than 90° (e.g., 100°, 110°, 120°, 130°, 140°, 150°, 160°, 170°, etc.). The angle 242 can be obtuse. The angle 242 can be the same as angle 142. In other embodiments, the angle 242 is different than angle 142 based on the manner in which the user is expected to hold the hand tool 100. The angle 242 can be selected to better complement the grip of the user (e.g., based on the anatomy of the human hand). Other configurations are possible.

The right section 202 can include a right hub 244. The right hub 244 can extend from the vertically extending portion 240. In some embodiments, the right hub 244 can be a unitary structure with the vertically extending portion 240 of the right handle 234. The right hub 244 and the right handle 232 can be monolithically formed.

In other embodiments, the right hub 244 is a separate component from the right handle 232. The vertically extending portion 240 can include a recess 246. The right hub 244 can be coupled to the recess 246 by welding, fasteners, glue, friction fit, pawl and ratchet, detent and protrusion, or other fixation method. In some embodiments, the right hub 244 is removable from the vertically extending portion 240. For instance, the right hub 244 can be removed to permit sterilization of the right tip 260. The right hub 244 can be removed to replace the right tip 260.

The right hub 244 can include a proximal portion 248. The proximal portion 248 of the right hub 244 can be received within the recess 246 of the vertically extending portion 240. The recess 246 can be shaped to complement the external surface of the right hub 244. The proximal portion 248 of the right hub 244 can be any cross-sectional shape including semi-circular, triangular, rectangular, etc. In some embodiments, the proximal portion 248 can extend the entire length of the vertically extending portion 240. The edge 250 of the proximal portion 248 can be angled to match the angle 242.

The right hub 244 can include a distal portion 252. The distal portion 252 can extend from the vertically extending portion 240. The distal portion 252 can extend from the recess 262 when proximal portion 248 is received within the recess 262. The edge 254 of the distal portion 252 can include a hub recess 256. The distal portion 252 can be a portion of a cylinder. The distal portion 252 can be any cross-sectional shape including semi-circular. In some embodiments, the distal portion 248 and the distal portion 252 have the same cross-sectional shape. In other embodiments, the proximal portion 248 and the distal portion 252 have different cross-sectional shapes. In some embodiments, the proximal portion 248 and the distal portion 252 can have the same diameter. In other embodiments, the proximal portion 248 and the distal portion 252 have different diameters.

The right hub 244 can define a right tip axis 258. The right tip axis 258 can be the axis upon which the right tip 260 rotates. The distal portion 252 of the right hub 244 can function to support the right tip 260 during rotation. The hub recess 256 can be aligned with the right tip axis 258. The hub recess 256 can function to maintain alignment of the right tip 260 during rotation. In some methods of assembly, the right hub 244 is coupled to the vertically extending portion 240. This can create a channel between the external surface of the right tip 260 and the internal surface of the recess 262. A portion of the right tip 260 can rotate within this channel.

The right tip 260 can include a proximal portion 264. The proximal portion 264 of the right tip 260 can be supported by the right hub 244. The proximal portion 264 of the right tip 260 can rotate about the right hub 244. At least a portion of the proximal portion 264 of the right tip 260 can be received within the recess 262 of the vertically extending portion 240.

In the illustrated embodiment, the recess 262 of the vertically extending portion 240 can include a first portion 266 and a second portion 268 (not shown). The first portion 266 can be similar or a mirror image of first portion 166. The second portion 268 can be similar or a mirror image of second portion 168. The first portion 266 can have a circular cross-section and the second portion 268 can have a circular cross-section. The first portion 266 can have a semi-circular cross-section and the second portion 268 can have a semi-circular cross-section. The cross-sectional shapes of the first portion 266 and the second portion 268 can permit free rotation of the right tip 260 within the recess 262.

The first portion 266 can have a first diameter and the second portion 268 can have a second diameter. The first diameter can be smaller than the second diameter. The first portion 266 can be located distal to the second portion 268. The first portion 266 of the recess 262 can be closer to the distal end 118. The second portion 268 can be located proximal to the first portion 266. The second portion 268 of the recess 262 can be closer to the proximal end 116. The difference in diameter between the first portion 266 and the second portion 268 of the recess 262 can create a lip.

The recess 262 can have any number of portions (e.g., two, three, four, five, six, etc.). Each portion can have a diameter that is either the same or different than one or more other portions. At least two of the portions have unequal diameters. Of the at least two portions, a portion near the distal end can have a smaller diameter than another portion near the proximal end. The difference in diameter between the portions of the recess 262 can create a lip.

In the illustrated embodiment, the right tip 260 can include a ridge 274 which can interact with the lip. The ridge 274 can extend from the external surface of the proximal portion 264 of the right tip 260. The ridge 274 can be sized to be received within the second portion 268 of the recess 262. For instance, the ridge 274 and the second portion 268 can have the same or similar diameter. The ridge 274 can have a larger diameter than the first portion 266. The ridge 274 can abut the lip created by the first portion 266 and the second portion 268. The ridge 274 can define axial translation of the right tip 260 when the right tip 260 is received within the recess 262. The ridge 274 can define the longitudinal movement of the right tip 260 when the ridge 274 is received within the recess 262. The ridge 274 can prevent disengagement between the vertically extending portion 240 and the right tip 260 by the application of axial force. Other shapes are considered to define axial translation (ridge, pin, etc.).

The proximal portion 164 of right tip 260 can include a right extension 278 which can interact with the hub 244. The right extension 278 can be a portion of a cylinder. In some embodiments, the right extension 278 can have a quarter-circular cross-section (e.g., encompasses 90 degrees). The right extension 278 can have a convex external surface. The convex external surface can be complementary to the second portion 268. The right extension 278 can have a concave internal surface 280. The concave internal surface 280 can be complementary to the external surface of the distal portion 252 of the right hub 244.

The proximal portion 264 of right tip 260 can include a protrusion 272 which can interact with the hub recess 256. The protrusion 272 is sized to be received within the hub recess 256. For instance, the protrusion 272 and the hub recess 256 can have the same or similar diameter. The protrusion 272 can extend along the right tip axis 258 when the ridge 274 is received within the recess 262. The protrusion 272 and the hub recess 256 can provide a pivot for the right tip 260 as the right tip 260 rotates.

The right tip 260 can include a distal portion 270. The distal portion 270 of the right tip 260 can include a longitudinally extending portion 282. The longitudinally extending portion 282 can be a portion of a cylinder. In some embodiments, the longitudinally extending portion 182 can have a semi-circular cross-section (e.g., encompasses 180 degrees). The longitudinally extending portion 282 can have a convex external surface. The distal 270 and longitudinally extending 282 portions can have other cross-sectional shapes (e.g., circular, elliptical, square, rectangular, triangular, polygonal, sigmoid, etc.).

The distal portion 270 of the right tip 260 can include a conical portion 286. The conical portion 286 can extend to a distal tip 288. The distal tip 288 can interact with the left section 102 to function as forceps. The conical portion 286 can include a cutting edge 290. The cutting edge 290 can interact with the left section 102 to function as scissors. The cutting edge 290 can be the same material as the distal portion 270 of the right tip 260. The cutting edge 290 can be the same material as the right tip 260. The cutting edge 290 can be a different material than the distal portion 270 of the right tip 260. The cutting edge 290 can be a different material than the right tip 260. The cutting edge 290 can be integrally or monolithically formed with the right tip 260. The cutting edge 290 can be a separate component and coupled to the right tip 260.

The distal portion 270 of the right tip 260 can have a flat internal surface 284. The flat internal surface 284 can be complementary to an internal surface of the left section 102. The flat internal surface 284 can extend the length of the longitudinally extending portion 282. The flat internal surface 284 can extend the length of the conical portion 286. The flat internal surface 284 can abut a flat internal surface of the left tip 160. Other cross-sectional shapes of the internal surface can be contemplated (e.g., circular, elliptical, square, rectangular, triangular, polygonal, sigmoid, etc.). These can be complimentary, mirror or rotationally similar to the right tip 260.

The distal portion 270 of the right tip 260 can include an electrode 292. In some embodiments, the longitudinally extending portion 282 can include the electrode 292. In some embodiments, the conical portion 286 can include the electrode 292. In some embodiments, the distal tip 288 can include the electrode 292. In some embodiments, the flat internal surface 284 can include the electrode 292. In some embodiments, the external surface of the right tip 260 can include the electrode 292. The electrode 292 can interact with the left section 102. The left section 102 can include a ground or another electrode. The right tip 260 can interact with the left section 102 function as an electrosurgical device. The electrode 292 can be activated by electrical energy supplied to the hand tool 100. The electrode 292 can be activated when the hand tool 100 is in the forceps configuration. In some embodiments, electrical energy is prevented from being supplied when the hand tool 100 is in the scissors configuration. The electrode 292 can be the same material as the distal portion 270 of the right tip 260. The electrode 292 can be the same material as the right tip 260. The electrode 292 can be a different material than the distal portion 270 of the right tip 260. The electrode 292 can be a different material than the right tip 260. The electrode 292 can be integrally or monolithically formed with the right tip 260. The electrode 292 can be a separate component and coupled to the right tip 260.

In some embodiments, the right lead 212 can pass through a channel in the right spring 224. The right lead 212 can pass through a channel in the right handle 232. The right lead 212 can pass through a channel in the right tip 260. The channels in any of the components in the right section 202 can be insulated.

In some methods of assembly, the right tip 260 is inserted within the recess 262. Then the right hub 244 is coupled to the vertically extending portion 240. The right tip 260 is place in the recess 262 prior to coupling of the right hub 244. The right tip 260 can be retained within the recess 262 by a retention mechanism (not shown). In some embodiments, the right hub 244 is removable. The right hub 244 can be removed to replace the right tip 260. The right hub 244 can be removed to sterilize the right tip 260.

In some methods of assembly, the right hub 244 is coupled to the vertically extending portion 240. This creates a channel between the external surface of the right hub 244 and the internal surface of the recess 262. In some embodiments, the right hub 244 is integrally formed with the vertically extending portion 240. Then the right tip 260 is inserted within the recess 262. The ridge 274 is aligned with the second portion 268 the recess 262 in the vertically extending portion 240. The internal surface 280 of the right extension 278 is aligned with the external surface of the right hub 244. The protrusion 272 of the right tip 260 is aligned with the hub recess 246.

From this position, the right tip 260 can be rotated about the right tip axis 258. The right tip 260 can be rotated until the ridge 274 is received within the second portion 268 of the recess 162. In this position, the internal surface 280 of the right extension 278 can be in contact with the external surface of the right hub 244. In this position, the protrusion 272 can be received within the hub recess 256.

As shown in FIG. 1, the hand tool 100 can include a pin 296 coupled to a portion of the right tip 260. The pin 296 can be positioned on the right extension 278. The pin 296 can extend from an external surface of the right extension 278. The pin 296 can extend radially outward from the outer surface of the right extension 278. In the illustrated embodiment, the pin 296 extends at an angle to the right tip axis 158. The angle may be substantially perpendicular or perpendicular. The pin 296 can extend transverse to the right tip axis 258.

The pin 296 can be a separate component coupled to the right tip 260. The pin 296 can be coupled by welding, fasteners, glue, friction fit, pawl and ratchet, detent and protrusion, or other fixation method. The pin 296 can be integrally or monolithically formed with the right tip 260. The pin 296 can interact with a mechanism 300, as discussed in greater detail below.

In an alternative embodiment, a pin can be coupled to a portion of the left tip 160 rather than the right tip 260. The pin can be a mirror image of the pin 296. The pin can be positioned on the left extension 178. The pin can extend from an external surface of the left extension 178. The pin can extend radially outward from the outer surface of the left extension 178. The pin 296 can be positioned on either extension 178, 278. The pin 296 can be positioned on either tip 160, 260.

In some embodiments, one of the tips 160, 260 can have a protrusion 294 and the other tip can have a recess 194. Referring to FIGS. 2B, 7C, and 8C, the left tip 160 can have the recess 194 and the right tip 260 can have the protrusion 294. In other embodiments, the left tip 160 can have the protrusion 294 and the right tip 260 can have the recess 194. The protrusion 294 can extend perpendicularly from the internal surface 284 of the right tip 260. The protrusion 294 can be located near the longitudinally extending portion 282 or the conical portion 286 of the right tip 260. The recess 194 can extend perpendicularly from the internal surface 184 of the left tip 160. The recess 194 can be located near the longitudinally extending portion 182 or the conical portion 186 of the left tip 160. The protrusion 294 and the recess 194 can be located near the distal end 118 of the hand tool 100.

The protrusion 294 can be sized to fit within the recess 194. The protrusion 294 or the recess 194 can include features to facilitate insertion of the protrusion 294 within the recess 194. In some embodiments, the edges of the protrusion 294 are rounded to facilitate insertion. The protrusion 294 can provide a pivot for the tips 160, 260 to rotate relative to each other. The protrusion 294 and the recess 194 can provide an axis 198 upon which the tips 160, 260 can pivot relative to each other. The protrusion 294 can engage the recess 194 when the hand tool 100 is in the scissor configuration. The protrusion 294 can engage the recess 194 when the hand tool 100 is in the intermediate configuration.

Each tip 160, 260 can include a cutting edge 190, 290. The cutting edges 190, 290 can be located on the conical portions 186, 286. The cutting edges 190, 290 can be located on the longitudinally extending portions 182, 282. Each tip 160, 260 can include one cutting edge, similar to a pair of scissors. The cutting edges 190, 290 can have a range of motion from a closed position to an open position. In some embodiments, the angle formed between the cutting edges 190, 290 is ninety degrees in the open position. When the cutting edges 190, 290 are being closed, the cutting edges 190, 290 can shear relative to each other. This action can cut tissue. In some embodiments, each tip 160, 260 can include two or more cutting edges.

The springs 124, 224 can be designed to return each handle 132, 232 to a neutral position. In some embodiments, the neutral position can include a separation between the conical portions 186, 286. In some embodiments, the neutral position can include a separation between the longitudinally extending portions 182, 282. In some embodiments, the neutral position can include a separation between the handles 132, 232. In other configurations, the hand tool 100 can include one spring (e.g., either the left spring 124 or the right spring 224). For instance, the hand tool 100 can include the right spring 224. The longitudinally extending portion 128 of the left handle 132 can extend to the mechanical connector 122. The right handle 232 can be manipulated to move the right tip 260 relative to the left tip 160.

In some embodiments, the longitudinally extending portions 128, 228 are curved or substantially curved (e.g., concave, convex, bent, etc.). In other configurations, the longitudinally extending portions 128, 228 are straight or substantially straight. In some embodiments, the conical portions 186, 286 are curved or substantially curved (e.g., concave, convex, bent, etc.). In other configurations, the conical portions 186, 286 are straight or substantially straight.

In some embodiments, the handles 132, 232 of the hand tool 100 can extend substantially along the longitudinal axis 106. The recesses 162, 262 can extend along the longitudinal axis 106. The handles 132, 232 can have any cross-sectional shape including rectangular, square, polygonal, etc. In some embodiments, the handles 132, 232 are straight or substantially straight. In some embodiments, the handles 132, 232 are curved or substantially curved (e.g., concave, convex, bent, etc.).

In some embodiments, electrical energy is supplied at a location along the length of the hand tool 100. For instance, electrical energy can be supplied to each handle 132, 232 of hand tool 100. The lead 112 can be coupled to the left handle 132 and the lead 212 can be coupled to the right handle 232. The distance between the handles 132, 232 can function as an electrical isolator. For instance, electrical energy can be supplied to each hub 144, 244 of hand tool 100. The lead 112 can be coupled to the left hub 144 and the lead 212 can be coupled to the right hub 244. The distance between the hubs 144, 244 can function as an electrical isolator. For instance, electrical energy can be supplied to each tip 160, 260 of hand tool 100. The lead 112 can be coupled to the left tip 160 and the lead 212 can be coupled to the right tip 260. The distance between the tips 160, 260 can function as an electrical isolator.

Each tip 160, 260 can include electrode 192, 292 for use in bipolar electrocautery for example. The electrodes 192, 292 can be located on the longitudinally extending portion 182, 282. The electrodes 192, 292 can be located on the conical portion 186, 286. The electrodes 192, 292 can be located on an external surface of the tips 160, 260. The electrodes 192, 292 can be located on an internal surface of the tips 160, 260 for instance the flat surfaces 184, 284. The electrodes 192, 292 can be configured for cauterization, hemostasis, and tissue dissection. Other modes of electrical current transmission are contemplated.

The hand tool 100 can allow current to flow from the location where electrical energy is supplied to the electrodes 192, 292. The hand tool 100 can have a current passage that allows current to flow through the hand tool 100 and to the electrodes 192, 292. The hand tool 100 can be sufficiently insulated to prevent the dissipation of electrical energy. The hand tool 100 can be grounded. The hand tool 100 can be designed to operate in conjunction with currently available current generators and other electrical devices.

The hand tool 100 can have a fluid passage having a fluid inlet and a fluid outlet. The fluid inlet can be located near a proximal end 116 of the hand tool 100. The fluid inlet can be connectable to a fluid source. The fluid outlet can be located near the distal end 118 of the hand tool 100. In some embodiments, the hand tool 100 can have more than one fluid outlet. The fluid outlet can be in fluid communication with the fluid inlet, such that fluid can travel through the fluid passage of the hand tool 100. The fluid outlet can be located on the longitudinally extending portion 182, 282. The fluid outlet can be located on the conical portion 186, 286. The fluid outlet can be located on an external surface of the tips 160, 260. The fluid outlet can be located on an internal surface of the tips 160, 260, for instance the flat surfaces 184, 284. The fluid outlet can be located near the electrodes 192, 292. The fluid can be a coolant, a medication, or any substance selected to be delivered to the surgical site. The hand tool 100 can be designed to operate in conjunction with currently available fluid systems.

Operation of the Hand Tool

The hand tool 100 can transition between at least three functional configurations, as shown generally in FIGS. 2A, 3, and 4. These configurations are referred to as the forceps configuration, the scissors configuration, and the probe configuration. In some embodiments, the forceps configuration includes a bipolar electrocautery forceps configuration. In some embodiments, the scissors configuration includes a microscissors configuration. In some embodiments, the scissors configuration and the forceps configuration are mutually exclusive functional configurations.

FIG. 2A shows the hand tool 100 in the forceps configuration. The springs 124, 224 bias the handles 132, 232 away from each other. The distal tips 188, 288 can be separated in the neutral position. The user can apply a force to the handles 132, 232 to move the distal tips 188, 288 toward each other. The user can release the force to the handles 132, 232 and the distal tips 188, 288 can return to the neutral position.

FIG. 3 shows the hand tool 100 in the intermediate configuration. In order to change configurations, the handles 132, 232 are moved toward each other. The user applies a force to overcome the biasing force of the springs 124, 224.

The internal surface of the handles 132, 232 can abut. The left tip 160 and the right tip 260 can be brought together. The tips 160, 260 can abut. The internal flat surfaces 184, 284 can abut. The left tip axis 158 and the right tip axis 258 can align along the longitudinal axis 106. The protrusion 294 can engage the recess 194. The intermediate configuration permits the transition from the forceps configuration to the scissors configuration. The intermediate configuration permits the transition from the scissors configuration to the forceps configuration. In some embodiments, the intermediate configuration is the probe configuration. In some embodiments, the hand tool 100 transitions from the forceps configuration to the probe configuration to the scissors configuration. In some embodiments, the hand tool 100 transitions from the scissors configuration to the probe configuration to the forceps configuration. In some embodiments, the probe configuration is not an intermediate configuration. In some embodiments, the hand tool 100 transitions from the scissors configuration to the forceps configuration to the probe configuration. In some embodiments, the hand tool 100 transitions from the forceps configuration to the scissors configuration to the probe configuration. In some embodiments, the intermediate configuration can permit the transition from the scissors configuration to the probe configuration. In some embodiments, the intermediate configuration can permit the transition from the probe configuration to the scissors configuration. In some embodiments, the intermediate configuration can permit the transition from the forceps configuration to the probe configuration. In some embodiments, the intermediate configuration can permit the transition from the probe configuration to the forceps configurations. The intermediate position permits the transition from the scissors configuration to the probe configuration, the probe configuration to the scissors configuration, the forceps configuration to the probe configuration, and the probe configuration to the forceps configurations.

FIG. 4 shows the hand tool 100 in the scissors configuration. The springs 124, 224 bias the handles 132, 232 away from each other. The distal tips 188, 288 can be separated in the neutral position. The user can apply a force to the handles 132, 232 to move the distal tips 188, 288 toward each other. The user can apply a force to the handles 132, 232 to pivot the distal tips 188, 288 about the axis 198. The user can apply a force to the handles 132, 232 to shear the cutting edges 190, 290 past each other. The user can release the force to the handles 132, 232 and the distal tips 188, 288 can return to the neutral position.

In the forceps, scissors, and probe configurations, the proximal portion 164 of the left tip 160 is retained within the recess 162. In both the forceps and the scissors configuration, the proximal portion 264 of the right tip 260 is retained within the recess 262. In both the forceps and the scissors configuration, the ridge 174 is retained within the recess 162. In both the forceps and the scissors configuration, the ridge 274 is retained within the recess 262.

In the forceps configuration, the internal flat surfaces 184, 284 are vertical or substantially vertical. In the scissors configuration, the internal flat surfaces 184, 284 are horizontal or substantially horizontal. In the forceps configuration, the right tip 260 can be horizontally offset from the left tip 160. The right tip 260 can be toward the right and the left tip 160 can be toward the left. In the scissors configuration, the right tip 260 can be generally over top the left tip 160. In the scissors configuration, the left tip 160 can be generally underneath the right tip 260. Other configurations are contemplated. For example, the internal surfaces of the tips can be vertical or substantially vertical in the scissors configuration and horizontal or substantially horizontal in the forceps configuration. The surfaces can be in any position in either the forceps or scissors configurations.

As shown in FIGS. 1-4, the hand tool 100 can include a mechanism 300 that enables the user to transition between the forceps configuration, the scissors configuration, and the probe configuration. In the illustrated embodiment, the mechanism 300 is located on the right handle 232. The mechanism 300 can interact with the pin 296. The mechanism 300 can be located as part of the same section as the pin 296. In the illustrated embodiment, the pin 296 is located on the right section 202. In the illustrated embodiment, the mechanism 300 is located on the right section 202.

The mechanism 300 can include a slide 302. The slide 302 can be coupled to the vertically extending portion 240. In the illustrated embodiment, the vertically extending portion 140 can include a retaining hole 298. The slide 302 can include a guide slot 310. The guide slot 310 can engage the retaining hole 298. For instance, the retaining hole 270 can engage a screw (not shown). The screw can translate within the guide slot 310 when the slide 302 translates. In some embodiments, the slide 302 can be coupled via a rail, protrusion, detent, ratchet, etc. The slide 302 is designed to translate along a portion of the vertically extending portion 240. The slide 302 is capable of sliding upward and downward relative to the right handle 232. The slide 302 can be less than the total height of the vertically extending portion 240 or a percentage of the total height (e.g., 20%, 30%, 40%, 50%, 60%, 70%, 80%, 90%, etc.). The slide 302 can be less than the total width of the vertically extending portion 240 or a percentage of the total width (e.g., 20%, 30%, 40%, 50%, 60%, 70%, 80%, 90%, etc.). The slide 302 can be greater than the total width of the vertically extending portion 240 (e.g., 110%, 120%, 130%, 140%, 150%, 160%, 170%, 180%, 190%, 200%, 300% etc.).

The slide 302 can include a lower portion 304 and an upper portion 306. The lower portion 304 can be approximately the same length as the vertically extending portion 240. The upper portion 306 can be a greater length than the vertically extending portion 240. The upper portion 306 can extend distally from the vertically extending portion 240 near the upper edge of the slide 302. In some embodiments, the upper portion 306 can include a housing 308. The housing 308 can extend distally from the vertically extending portion 240 near the upper edge of the slide 302. The housing 308 can have a greater width than the width of the lower portion 304. The housing 308 can be convex. The housing 308 can have a non-symmetrical shape. In the illustrated embodiment, the slide 302 can include at least a portion that extends distally from the vertically extending portion 240. The housing 308 can include any shape (e.g., circular, elliptical, square, rectangular, triangular, polygonal, sigmoid, etc.).

The mechanism 300 can include a grip 312. The grip 312 can be located near an edge of the slide 302. The grip 312 can be located proximally from the vertically extending portion 240. In the illustrated embodiment, the grip 312 is located near the proximal end of the slide 302. Other configurations are contemplated (e.g., near the top of the slide 302, near the bottom of the slide 302, on an external surface of the slide 302, etc.). The grip 312 can include one or more ridges to facilitate the movement of the slide 302. Other configurations are contemplated (e.g., roughened surfaces, protrusions, etc.).

The mechanism 300 can include a slot 314. The slot 314 provides a path for the pin 296 as the slide 302 is translated.

The slot 314 can be within the housing 308. The outer perimeter of the slot 314 can be within or smaller than the outer perimeter of the housing 308. The housing 308 can have a width sufficient to enclose the pin 296. The housing 308 can have an area of increased thickness near the slot 314. The increased thickness can facilitate repeated movements against the pin 296 without deformation of the housing 308. In some embodiments, the slot 314 is covered. The slot 314 can be covered by an external surface of the housing 308. In other embodiments, the slot 314 is exposed to the user.

In some embodiments, the slot 314 is linear. In other embodiments, the slot 314 is non-linear. The slot 314 can have a variety of shapes including curved, s-shaped, bow-tie shaped, sloped, stepped, etc. The slot 314 can have any shape that allows the slot 314 to function as a guide for the pin 296. The slot 314 can be integrally formed with the slide 302. The slot 314 can be formed by any machining, casting or forming processes.

The slot 314 can function to guide the pin 296. The pin 296, as discussed above, is coupled to the right tip 260. In the illustrated embodiment, the pin 296 extends from an external surface of the right extension 278. An edge of the slot 314 pushes the pin 296 as the slide 302 is moved. The shape of the slot 314 permits the pin to rotate about the right tip axis 258 as the slide 302 is moved. In some embodiments, the pin 296 can be adjusted to a number of discrete positions within the slot 314 (e.g., two, three, four, five, etc.). In some embodiments, the pin 296 can be adjusted to an infinite number of positions within the slot 314.

The slide 302 can be coupled to the hand tool 100 at two points of contact. The slide 302 can be coupled to the vertically extending portion 140 with the retaining hole 298 and the guide 310. The slide 302 can be coupled to the tip 260 with the pin 296 and the slot 314. As the slide 302 translates, the screw (not shown) in the retaining hole 298 translates within the guide 310. As the slide 302 translates, the pin 296 translates within the slot 314.

The mechanism 300 can have a first position and a second position. The first position can correspond to forceps configuration. The second position can correspond to the scissor configuration. In the illustrated embodiments, the mechanism 300 can be in the first position when the slide 302 is lower on the vertically extending portion 240. There can be a larger separation between the top surface of the slide 302 and the top surface of the vertically extending portion 240. There can be a smaller separation between the bottom surface of the slide 302 and the bottom surface of the vertically extending portion 240. The bottom surface of the slide 302 and the bottom surface of the vertically extending portion 240 can be aligned. FIG. 2A shows the mechanism 300 in the first position. When the mechanism 300 is in the first position, the left tip 160 and the right tip 260 can be used as forceps.

In the illustrated embodiments, the mechanism 300 can be in the second position when the slide 302 is higher on the vertically extending portion 240. There can be a smaller separation between the top surface of the slide 302 and the top surface of the vertically extending portion 240. The top surface of the slide 302 and the top surface of the vertically extending portion 240 can be aligned. There can be a larger separation between the bottom surface of the slide 302 and the bottom surface of the vertically extending portion 240. FIG. 4 shows the mechanism 300 in the second position. When the mechanism 300 is in the second position, the left tip 160 and the right tip 260 can be used as scissors.

Figure 5A:
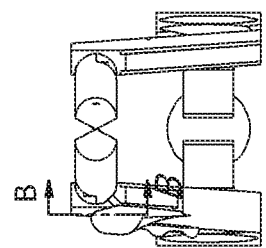
FIG. 5A is a front view of the hand tool of FIG. 1 in the forceps configuration.

FIGS. 5A and 5B show the mechanism 300 in the first position. FIG. 5A shows the front view of the hand tool 100 and FIG. 5B shows a cross-section view along line B-B. In the first position, the pin 296 is near the lower end of the slot 314. The pin 296 is retained within the slot 314. In the illustrated embodiment, the pin 296 is not being acted on by any edge of the slot 314.

Figure 6A:
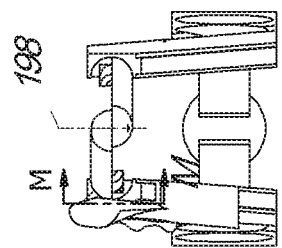
FIG. 6A is a front view of the hand tool of FIG. 1 in the scissors configuration.

FIGS. 6A and 6B show the mechanism 300 in the second position. FIG. 6A shows the front view of the hand tool 100 and FIG. 6B shows a cross-section view along line M-M. In the second position, the pin 296 is near the upper end of the slot 314. As the slide 302 is moved upward along the vertically extending portion 240, an edge of the slot 314 can come into contact with the pin 296. Further upward movement of the slide 302 can cause the edge of the slot 314 to exert a force on the pin 296. This force can cause the pin 296 to rotate about the right tip axis 258. Further upward movement of the slide 302 can cause the pin to rotate a quarter turn (e.g., 90°) or approximately a quarter turn (e.g., 80°, 85°, 90°, 95°, 100°, etc.). Rotation of the pin 296 can cause the right tip 260 to rotate within the recess 262 of the vertically extending portion 240. Rotation of the right tip 260 can exert a force on the left tip 160. The force exerted by the right tip 260 can be directly exerted on the left tip 160. As the right tip 260 is rotated within the recess 262, the left tip 160 can rotate within the recess 162.

Figure 7A:
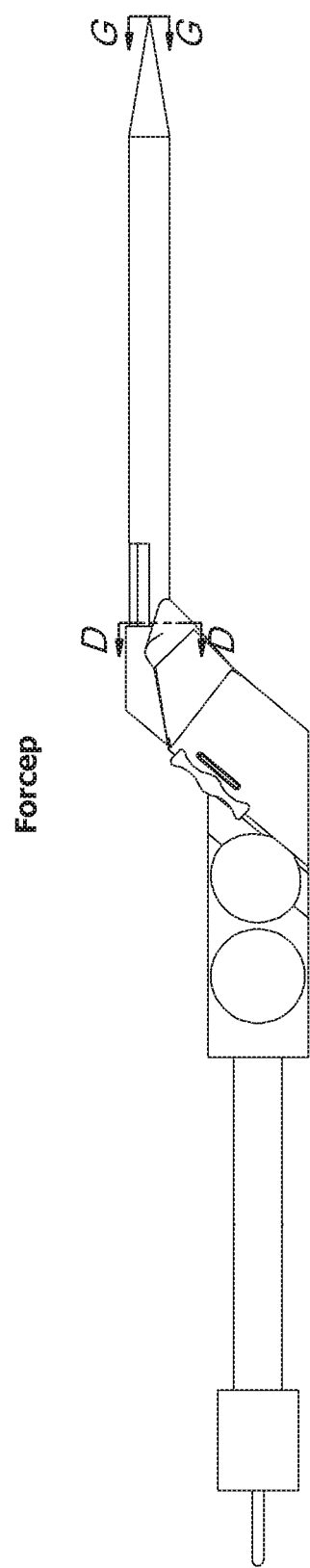
FIG. 7A is a side view of the hand tool of FIG. 1 in the forceps configuration.
Figure 7C:
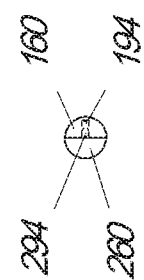
FIG. 7C is a cross-sectional view taken along line G-G in FIG. 7A.
Figure 7B:
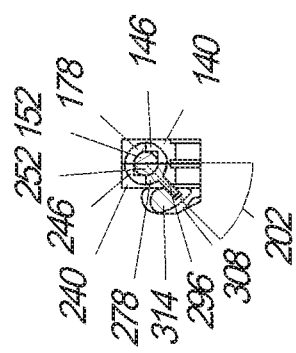
FIG. 7B is a cross-sectional view taken along line D-D in FIG. 7A.
Figure 8C:
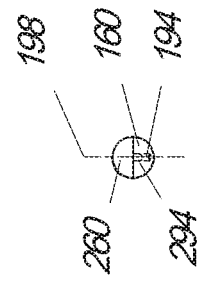
FIG. 8C is a cross-sectional view taken along line T-T in FIG. 8A.

FIGS. 7A-7C show the mechanism 300 in the first position. FIG. 7A shows the side view of the hand tool 100. FIG. 7B shows a cross-section view along line D-D. FIG. 7C shows a cross-section view along line G-G. In the illustrated embodiment, the first position corresponds to the slide 302 being in a lower position as shown in FIG. 7A.

The pin 296 can extend from the right extension 278 as shown in FIG. 7B. The pin 296 can be retained within the slot 314. In the illustrated embodiment, the slot 314 is formed in a portion of the housing 308. The pin 296 can have a sufficient size to extend past the vertically extending portion 240 and into the housing 308. The pin 296 can have a greater dimension than the width of the vertically extending portion 240. The pin 296 can be positioned at an angle 202. The angle 202 can be approximately 45° from the vertical plane of the hand tool 100. Other angles are possible (e.g., 0°, 5°, 10°, 15°, 20°, 25°, 30°, 35°, 40°, 45°, 50°, 55°, 60°, 65°, 70°, 75°, 80°, 85°, 90°, etc.). The protrusion 294 can be received in the recess 194 as shown in FIG. 7C.

Figure 8B:
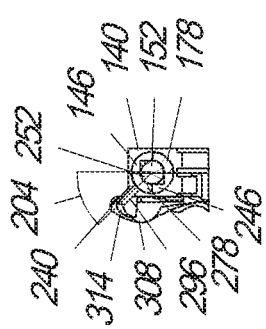
FIG. 8B is a cross-sectional view taken along line P-P in FIG. 8A.

FIGS. 8A-8C show the mechanism 300 in the second position. FIG. 8A shows the side view of the hand tool 100. FIG. 8B shows a cross-section view along line P-P. FIG. 8C shows a cross-section view along line T-T. In the illustrated embodiment, the second position corresponds to the slide 302 being in a higher position as shown in FIG. 8A.

The pin 296 can be rotated as shown in FIG. 8B. The pin 296 can be positioned at an angle 204. The angle 204 can be approximately 45° from the vertical plane of the hand tool 100. Other angles are possible (e.g., 0°, 5°, 10°, 15°, 20°, 25°, 30°, 35°, 40°, 45°, 50°, 55°, 60°, 65°, 70°, 75°, 80°, 85°, 90°, etc.) The pin 296 can rotate approximately 90° as the mechanism 300 is moved from the first position to the second position. The pin 296 can rotate approximately 90° as the hand tool 100 is transitioned between the forceps configuration and the scissors configuration. Other ranges of motion of the pin 296 are possible (e.g., 80°, 85°, 90°, 95°, 100°).

The protrusion 294 can be received in the recess 194 as shown in FIG. 8C. The protrusion 294 can extend from the internal flat surface 284 of the right tip 260. The recess 194 can extend into the internal flat surface 184 of the left tip 160. The tips 160, 260 can rotate or pivot about the protrusion 294. The tips 160, 260 can rotate or pivot about the axis 198. The protrusion 294 can extend downward such that gravity aids in the retention of the protrusion 294 within the recess 194.

The functional configuration of the hand tool 100 is selected by the user by manipulating the mechanism 300. The user can slide a finger to move the slide 302. The user can manipulate the mechanism 300 while holding the hand tool 100. The slide 302 can change the position of the slot 314 relative to the pin 296. The mechanism 300 can exert a force on the pin 296 to rotate the pin 296. In the illustrated embodiment, an edge of the slot 314 of the mechanism 300 can act on the pin 296. The rotation of the pin 296 can rotate both tips 160, 260. The tips 160, 260 can rotate approximately 90° as the hand tool 100 is transitioned between the forceps configuration and the scissors configuration. Other ranges of motion of the tips 160, 260 are possible (e.g., 80°, 85°, 90°, 95°, 100°).

The mechanism 300 can convert translational motion of the slide 302 into rotational motion of pin 296. When the slide 302 is moved upward, the mechanism 300 can apply a rotational force to the pin 296. The pin 296 can be coupled to the right extension 278. The right extension 278 can have a cross-sectional shape of roughly a quarter-circle. The right extension 278 can rotate within the recess 262 of the vertically extending portion 240 as the pin 296 is rotated. The right extension 278 can rotate about the right hub 244 as the pin 296 is rotated. The right hub 244 can provide support to the right tip 260 as the pin 296 is rotated. The protrusion 272 and the hub recess 256 can maintain alignment of the right tip 260 as the right tip 260 is rotated. The right tip 260 can rotate about the right tip axis 258. The right tip 260 can rotate about the longitudinal axis 106.

The left extension 178 can have a cross-sectional shape of roughly a quarter-circle. The left extension 178 can rotate within the recess 162 of the vertically extending portion 140 as the pin 296 is rotated. The left extension 178 can rotate about the left hub 144 as the pin 296 is rotated. The left hub 144 can provide support to the left tip 160 as the pin 296 is rotated. The protrusion 172 and the hub recess 156 can maintain alignment of the left tip 160 as the left tip 160 is rotated. The left tip 160 can rotate about the left tip axis 158. The left tip 160 can rotate about the longitudinal axis 106.

Both tips 160, 260 can rotate the same direction. In the illustrated embodiment, the right tip 260 rotates clockwise along the right hub 244 when the hand tool 100 transitions from the forceps configuration to the scissors configuration. The right tip 260 rotates counter-clockwise along the right hub 244 when the hand tool 100 transitions from the scissors configuration to the forceps configuration. In the illustrated embodiment, the left tip 160 rotates clockwise along the left hub 144 when the hand tool 100 transitions from the forceps configuration to the scissors configuration. The left tip 160 rotates counter-clockwise along the left hub 144 when the hand tool 100 transitions from the scissors configuration to the forceps configuration. The rotation in the clockwise direction is shown in FIGS. 7B and 8B. Other configurations are possible, where the mechanism rotates the tips clockwise to embody the transitions from the scissors configuration to the forceps configuration and counterclockwise to transitions from the forceps configuration to the scissors configuration.

In some embodiments, one mechanism 300 is provided. In the illustrated embodiment, the mechanism 300 is coupled to the right handle 232 and the pin 296 is provided on the right tip 260. The right tip 260 is the leader and the left tip 160 is the follower. The tips 160, 260 can be brought together and into contact in the intermediate configuration. In the intermediate configuration, movement of the right tip 260 can impart a force on the left tip 160 to cause rotation. In some embodiments, the mechanism 300 is coupled to the left handle 132 and the pin 296 is provided on the left tip 160. The left tip 160 can be the leader and the right tip 260 can be the follower. In some embodiments, more than one mechanism 300 is provided. One mechanism 300 is coupled to the right handle 232 and the pin 296 is provided on the right tip 260. Another mechanism is coupled to the left handle 132 and another pin is provided on the left tip 160. The user can move one or both mechanisms 300 to rotate the tips 160, 260.

The user selects the configuration of the hand tool 100 by movement of the mechanism 300. In some embodiments, the mechanism 300 is moved by a finger of the hand in which the hand tool 100 is held. In some embodiments, the mechanism 300 is moved by the thumb of the hand in which the hand tool 100 is held. In some embodiments, the mechanism 300 is moved by a finger or thumb of the hand not holding the hand tool 100. The mechanism 300 allows the user to select between functional configurations with relative ease. The movement of the mechanism 300 can be intuitive to the user.

The hand tool 100 does not need to be removed from the surgical site to switch configurations. The mechanism 300 can be manipulated while the tips 160, 260 remain within the surgical site. The hand tool 100 requires the user to collapse the hand tool 100 in the intermediate configuration. This requires less space than either the forceps configuration or the scissors configuration. In some embodiments, once in the intermediate configuration, the user can transition between the forceps configuration and the scissors configuration. In some embodiments, once in the intermediate configuration, the user can transition between the forceps configuration, the scissors configuration, and the probe configuration. The hand tool 100 does not require any large movements to switch configurations.

Once the hand tool 100 is in the desired configuration, the scissors or forceps are operated conventionally. In the forceps configuration, movement of the handles 132, 232 causes the forceps to come together. The springs 124, 224 can return the handles 132, 232 to a neutral position. In the scissors configuration, movement of the handles 132, 232 causes the cutting edges of the tips 160, 260 to shear with respect to each other. The springs 124, 224 return the handles 132, 232 to a neutral position.

Component to Facilitate Scissor Function

The hand tool 100 can include a component to maintain alignment of the tips 160, 260 in the scissors configuration. This component can ensure engagement between the cutting edges 190, 290 to allow the tips 160, 260 to cut tissue. In the illustrated embodiment, the component is a sleeve 400. The sleeve 400 can extend along the length of one of the tips 160, 260 in the forceps configuration. The sleeve 400 can extend along the length of both tips 160, 260 in the scissors configuration. Other mechanisms are contemplated which function to hold the tips 160, 260 together in the scissors configuration.

FIGS. 9A-9D show an embodiment of the sleeve 400. FIG. 9A shows the perspective view of the hand tool 100 with the sleeve 400. FIG. 9B shows a top view and FIG. 9C shows a side view. FIG. 9D shows a cross-section view along line K-K. In FIG. 9A, the right handle 232 is removed.

The sleeve 400 is coupled to the left handle 132. The sleeve 400 can be coupled to the left handle 132 by welding, fasteners, glue, friction fit, pawl and ratchet, detent and protrusion, or other fixation method. In the illustrated embodiment, the sleeve 400 is coupled to the vertically extending portion 140. The sleeve 400 extends from the vertically extending portion 140. The sleeve 400 extends along the left tip axis 158.

The sleeve 400 can include a proximal portion 402 near the vertically extending portion 140. The proximal portion 402 can be flat or substantially flat. The proximal portion 402 can be offset from the left tip 160. In some embodiments, the proximal portion 402 is not in contact with the left tip 160.

The sleeve 400 can include a distal portion 404. The distal portion 404 can have an internal surface 406 and an external surface 408. The internal surface 406 can be concave. The internal surface 406 can be sized to complement the external shape of the left tip 160. The diameter of the internal surface 406 can be equal or approximately equal to the diameter of the left tip 160. The diameter of the internal surface 406 can be slightly larger than the diameter of the external surface of the left tip 160 or a percentage thereof (e.g., 105%, 110%, 115%, 120%, 125%, 130%, 140%, 145%, 150%, etc.). The internal surface 406 can complement the external shape of the left tip 160 in the forceps configuration. The internal surface 406 can also complement the external shape of a portion of the left tip 160 and a portion of the right tip 260 in the scissors configuration. The external surface 408 of the distal portion 404 can be convex. The external surface 408 can have any shape (e.g., elliptical, oval, rectangular, square, etc.).

The sleeve 400 can include a middle portion 410 that transitions between the proximal portion 402 and the distal portion 404. The sleeve 400 can be tapered as shown in FIG. 9B. The proximal portion 402 can surround a smaller portion of the left tip 160. The distal portion 404 can surround a larger portion of the left tip 160.

The sleeve 400 can extend along a portion of the tip 160. In the illustrated embodiment, the conical portion 186 extends distally from the sleeve 400 as shown in FIG. 9C. The sleeve 400 is sized to permit movement of the tips 160, 260 in the forceps configuration and the scissors configuration.

In the forceps configuration (not shown), the distal portion 404 surrounds the left tip 160. The internal surface 406 can be adjacent to the left tip 106. The internal surface 406 can be in contact with or abut the left tip 106. The distal portion 404 can surround the entire left tip 160 or a portion thereof. The distal portion 404 can extend beyond the left tip 160. In the illustrated embodiment, the distal portion 404 can be semi-circular. The left tip 160 can be semi-circular.

In the scissors configuration shown in FIG. 9D, the distal portion 404 surrounds a portion of the left tip 160 and a portion of the right tip 260. The internal surface 406 can be adjacent to a portion of the left tip 160 and a portion of the right tip 260. The internal surface 406 can be in contact with or abut a portion of the left tip 160 and a portion of the right tip 260. The distal portion 404 can surround a percentage of the left tip 160 (e.g., 30%, 40%, 50%, 60%, 70%, etc.). The distal portion 404 can surround a percentage of the right tip 260 (e.g., 30%, 40%, 50%, 60%, 70%, etc.). The distal portion 404 can surround half of the left tip 160 and half of the right tip 260. In the illustrated embodiment, the internal surface 406 can be semi-circular. The external surface of the left tip 160 and the right tip 260 can be semi-circular. The internal surface 406 can allow the free rotation of the left tip 160 and the right tip 260 there within. The internal surface 406 can take other shapes or combination of shapes (e.g., semi-circular and flat, rectangular, circular, elliptical, square, rectangular, triangular, polygonal, sigmoid, etc.).

FIG. 9D shows the sleeve 400 contacting both tips 160, 260 in the scissors configuration. The sleeve 400 can function to hold the tips 160, 260 together in the scissors configuration. The sleeve 400 can function to prevent separation of the tips 160, 260 in the scissors configuration. The sleeve 400 can function to prevent separation of the protrusion 294 and the recess 194 in the scissors configuration. The movement of the right tip 260 upward is reduced or prevented by the sleeve 400. The movement of the left tip 160 downward is reduced or prevented by the sleeve 400. Other mechanisms are contemplated which function to hold the tips 160, 260 together in the scissors configuration.

Locking Component to Maintain Functional Configuration

The hand tool 100 can include a locking mechanism 500. The locking mechanism 500 can function to reduce or prevent rotational movement of one or more of the extensions 178, 278. The locking mechanism 500 can function to reduce or prevent rotational movement of one or more of the tips 160, 260. The locking mechanism 500 can be locked when the hand tool 100 is in the forceps configuration, as shown in FIG. 2A. The locking mechanism 500 can be locked when the hand tool 100 is in the scissors configuration, as shown in FIG. 4. The locking mechanism 500 can be unlocked when the hand tool 100 is in the intermediate configuration, as shown in FIG. 3.

Figure 10A:
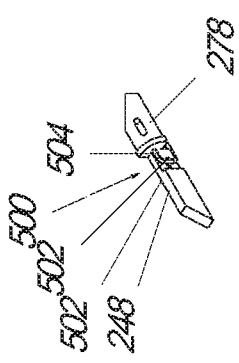
FIG. 10A is a perspective view of the hand tool in the scissors configuration with a locking mechanism.
Figure 10B:
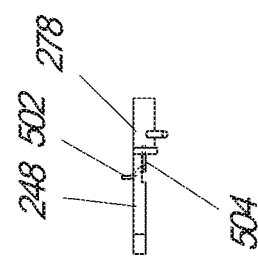
FIG. 10B is a top view of the hand tool of FIG. 10A.
Figure 10C:
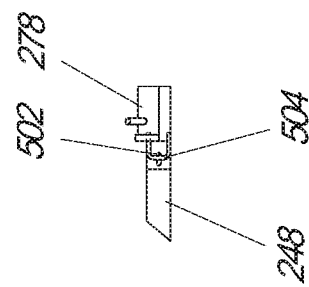
FIG. 10C is a side view of the hand tool of FIG. 10A.
Figure 12A:
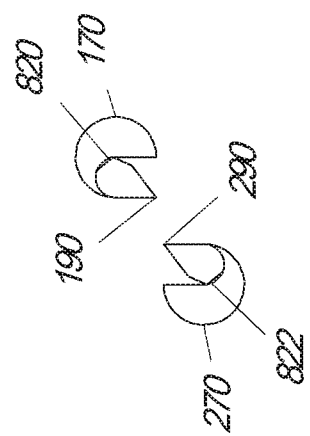
Figure 12B:
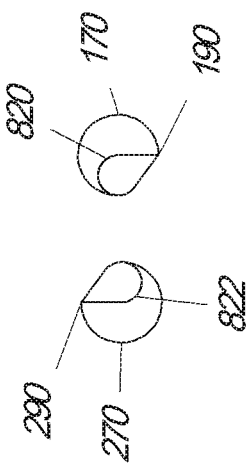
Figure 16:
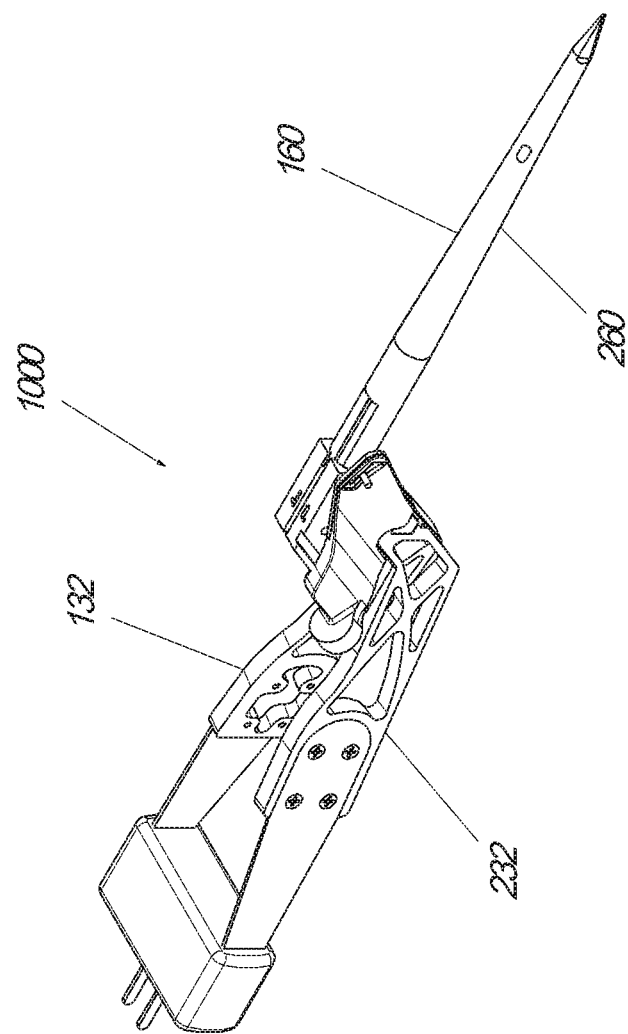

FIGS. 10A-10C show an embodiment of the locking mechanism 500. The locking mechanism 500 can include a bar 502. The bar 502 can be any shape (e.g., straight, curved, bent, s-shape etc.). In the illustrated embodiment, the bar 502 has a bend. The bar 502 can be retained within a slot. The bar 502 can move within the slot in a direction perpendicular or substantially perpendicular to the right tip axis 258. In the illustrated embodiment, the slot can be located in the right hub 244. The slot can be located in the proximal portion 248 or the distal portion 252 of the right hub 244. In the illustrated embodiment, the slot can be located in the proximal portion 248. In some embodiments, the slot is within the right handle 232.

The bar 502 can be coupled to a pin 504. The pin 504 can be any shape (e.g., curved, straight, u-shaped, slanted, etc.). In the illustrated embodiment, the pin 504 is u-shaped. The pin 504 can include a proximal end which engages the bar 502. The pin 504 can include a distal end which engages the extension 278. In the illustrated embodiment, the pin 504 can engage a recess in the extension 278. In the illustrated embodiment, the pin 504 has two prongs. The upper prong of the pin 504 can engage the recess when the hand tool 100 is in the scissors configuration, as shown in FIGS. 10A-10C. The lower prong of the pin 504 can engage the recess when the hand tool 100 is in the forceps configuration. The pin 504 can prevent rotation of the extension 278 when a prong of the pin 504 engages the recess of the extension 278.

The bar 502 can extend from an internal surface of the handle 232. The action of abutting the handles 132, 232 can cause the bar 502 to move within the slot. This action can unlock the locking mechanism 500. The locking mechanism 500 can be unlocked when the handles 132, 232 are brought toward each other. In some embodiments, the left handle 132 will exert a force on the bar 502. In some embodiments, the hub 144 will exert a force on the bar 502. The bar 502 can move outward from the longitudinal axis 106. The bar 502 can move toward the handle 232. The shape of the bar 502 can cause the pin 504 to be moved along the right tip axis 258. The pin 504 can translate toward the proximal end 116 as the bar 502 is moved toward the handle 232. The pin 504 can disengage the recess of the extension 278 when the pin 504 translates proximally. The upper prong of the pin 504 can disengage the recess when the pin 504 translates proximally. The lower prong of the pin 504 can disengage the recess when the pin 504 translates proximally. The tips 160, 260 can be rotated when the pin 504 disengages the recess in the right extension 278.

The locking mechanism 500 can have a neutral position. The neutral position can be the locked position. In the neutral position, a prong of the pin 504 can engage the recess in the extension 278. The locking mechanism 500 can return to the neutral position via a spring. In other embodiments, the locking mechanism 500 can be returned to the neutral position by other means (e.g., magnets, gravity, manually force, etc.). The locking mechanism 500 can be manually moved by the user. The locking mechanism 500 can be returned to the neutral position by the action of separating the handles 132, 232.

In some embodiments, the locking mechanism 500 is placed within the recess 262 in the vertically extending portion 240. The locking mechanism 500 would block the rotational movement of the right extension 278 in the recess 262. In some embodiments, the locking mechanism 500 is placed within the recess 162 in the vertically extending portion 140. The locking mechanism 500 would block the rotational movement of the left extension 178 in the recess 162. In some embodiments, the locking mechanism 500 can remain in one recess 162, 262. In some embodiments, a locking mechanism 500 can be provided for each recess 162, 262. In some embodiments, the locking mechanism 500 can move between the recesses 162, 262. For instance, the locking mechanism 500 can be located in the recess 262 when the hand tool 100 is in the forceps configuration. The locking mechanism 500 can rotate into the recess 162 when the hand tool 100 is in the scissors configuration.

In the illustrated embodiment, the locking mechanism 500 can be included in the right section 202. In some embodiments, the locking mechanism 500 can be included in the left section 102. In some embodiments, the locking mechanism 500 can be included in both the left section 102 and the right section 202. Other embodiments are contemplated to prevent the extensions 178, 278 from rotating (e.g., spring, detent, magnet, etc.).

In other embodiments, the user can manipulate an interface (not shown) to unlock the locking mechanism 500. The neutral position can be that the locking mechanism 500 is locked. For instance, the interface (not shown) can be a button that when depressed would unlock the locking mechanism 500. The interface (not shown) can be a slide that can have a position when the locking mechanism 500 is locked and a position when the locking mechanism 500 is unlocked. Other configurations of interfaces (not shown) are contemplated.

The hand tool 100 can be generally composed of metal alloys, plastic, or other suitable biocompatible material. The hand tool 100 can be made by conventional machining and metal fabrication techniques, plastic fabrication techniques, and finishing processes including but not limited to milling, lathing, electro discharge and welding, injection molding, powder coating and painting. The hand tool 100 can be optionally coated with one or more coatings, including but not limited to plastic, rubber, powder coat and paint or any combination thereof. The hand tool 100 can comprise multiple parts assembled and delivered to its intended user. The hand tool 100 can be sterilized before it is provided to the intended user.

Different methods of switching configurations, different mechanism for rotating the tips, different configurations of the pin are contemplated. Further, the hand tool 100 may be configured to provide different tool functions than forceps and scissors described herein. Further, the hand tool 100 may have additional functional configurations corresponding to different tools. The hand tool 100 may be used in conjunction with other tools, for instance an operating microscope.

Other embodiments of the hand tool are shown in U.S. Provisional Patent Application No. 61/906,337 filed Nov. 19, 2013, the disclosures of which is incorporated by reference herein in its entirety. The hand tool 100 described herein can have any of the features, components, or subcomponents described in the provisional application. In the illustrated embodiment of FIGS. 1-9 in the provisional application, the handle 132 can include an additional longitudinally extending portion located distal of the vertically extending portions 140, 240. This additional longitudinally extending portion is shown in FIGS. 1-3 of U.S. Provisional Patent Application No. 61/906,337. The additional longitudinally extending portion of the left handle 132 can include the recess 162. The recess 162 can be enclosed or partially enclosed by the additional longitudinally extending portion. The recess 162 can be semi-circular as described herein. The recess 162 can be sized to receive the left extension 178.

In some embodiments, the right handle 232 can be a mirror image of the left handle 132. The right handle 232 can include an additional longitudinally extending portion. The additional longitudinally extending portion can include the recess 262. The recess 262 can be enclosed or partially enclosed by the additional longitudinally extending portion. The recess 262 can be semi-circular as describe herein. The recess 262 can be sized to receive the right extension 278.

The tips 160, 260 can include a respective longitudinally extending portion 182, 282, as shown in FIG. 5 of U.S. Provisional Patent Application No. 61/906,337. The longitudinally extending portion 182, 282 can be semi-circular. The tips 160, 260 can include a respective conical portion 186, 286. The tips 160, 260 can include a respective extension 178, 278. The extensions 178, 278 can be quarter-circular. At least one of the extensions 178, 278 can include an engaging surface. The engaging surface can be a pin. The pin can extend parallel or substantially parallel to the tip axis 158, 258. The engaging surface can be rotated to the extensions 178, 278 within the recesses 162, 262. The engaging surface can be rotated to transition the hand tool between a forceps configuration and a scissors configuration.

The mechanism 300 can include a slide 302 as shown in FIG. 6 of U.S. Provisional Patent Application No. 61/906, 337. The slide 302 can include a slot 314 configured to interact with the pin. The slide is configured to move upward and downward. The movement of the slide can rotate the engaging surface. The engaging surface can rotate the extension 178, 278 to which the engaging surface is attached. The extension can rotate one of the tips 160, 260 which can impart a force of the other of the tips 160, 260.

FIGS. 16-26 show an embodiment of a hand tool 1000. The hand tool 1000 can include features of hand tool 100 and similar reference numbers are used for similar features. The two tips 160, 260 of the hand tool 100 have been described herein. In some embodiments, the tips 160, 260 are brought together. Each of the bilateral tips 160, 260 can have an axis 158, 258 about which each tip rotates. The tips 160, 260 can be brought together to align their axes 158, 258. Alignment of the bilateral tip axes 158, 258 can facilitate rotation of the tips 160, 260. Rotation of the tips 160, 260 can allow the hand tool 100, 1000 to transition between functional configurations.

The hand tool 100, 1000 has the longitudinal axis 106 that extends between the proximal end 116 and the distal end 118. In some embodiments, the axis 158, 258 are aligned along the longitudinal axis 106 when the tips 160, 260 are brought together. In some embodiments, the tips 160, 260 rotate about the longitudinal axis 106 of the hand tool 100, 1000. In other embodiments, the axis 158, 258 are not aligned along the longitudinal axis 106 when the tips 160, 260 are brought together. In some embodiments, the tips 160, 260 rotate about another axis which is at an angle or skewed relative to the longitudinal axis 106 of the hand tool 100, 1000.

In some embodiments, the tips 160, 260 can rotate along multiple axes. For instance, the left tip 160 can rotate about left tip axis 158. In some embodiments, the left tip axis 158 is a longitudinal axis of the left tip 160. In other embodiments, the left tip axis 158 is at an angle or skewed relative to the longitudinal axis of the left tip 160. The right tip 260 can rotate about right tip axis 258. In some embodiments, the right tip axis 258 is a longitudinal axis of the right tip 260. In other embodiments, the right tip axis 258 is at an angle or skewed relative to the longitudinal axis of the right tip 260. The tips 160, 260 can rotate along their axes 158, 258 in the same direction. The tips 160, 260 can rotate along their axes 158, 258 in an opposite direction.

In some embodiments, the left tip axis 158 and the right tip axis 258 are aligned when the tips 160, 260 are brought together. In some embodiments, the tips can rotate about the aligned axes. In some embodiments, each tip 160, 260 has multiple axes of rotation. In some embodiments, the tips can rotate about the aligned axes while simultaneously rotating about non-aligned axes. The tips 160, 260 can rotate along their non-aligned axes in the same or opposite direction as rotation about the aligned axis. Any portion or all of a tip 160, 260 can be made to rotate in any direction.

In some embodiments, the hand tool 100, 1000 includes rotation of tips 160, 260 about an axis that is not common between the two tips 160, 260. In some embodiments, the two tips 160, 260 can rotate along independent axes (>1 axis). In some embodiments, the two tips 160, 260 would rotate in same or opposite direction along independent axes (>1 axis). In some embodiments, the two tips 160, 260 would rotate in same or opposite direction along independent axes (>1 axis) in addition to rotating simultaneously on a common axis. In some embodiments, the two tips 160, 260 would rotate along independent axes (>1 axis) in addition to rotating in same or opposite direction simultaneously on a common axis. In some embodiments, the hand tool 100, 1000 includes multiple axes for rotation. In some embodiments, the axes for rotation are aligned with components of the hand tool 100, 1000. In other embodiments, the axes for rotation are separate from the components of the hand tool 100, 1000.

In some embodiments, the rotation of the two tips 160, 260 along the same or independent axes could facilitate change from an exclusively/predominantly electrode surface to an exclusively/predominantly cutting edge. In some embodiments, the rotation of the two tips 160, 260 along the same or independent axes allows no contact of the cutting edge to tissue while cauterizing and no contact of the cauterizing surface while cutting. In some embodiments, the rotation of the two tips 160, 260 along the same or independent axes prevents or limits contact of the cutting edge to tissue while cauterizing. In some embodiments, the rotation of the two tips 160, 260 along the same or independent axes prevents or limits contact of the cauterizing surface while cutting.

FIGS. 11A-11E shows one illustration of the movement of the tips. FIG. 11A shows the tips 160, 260 in a forceps configuration. Axis 276 corresponds to the longitudinal axis of the tip 260, Axis 176 corresponds to the longitudinal axis of the tip 160, and Axis 106 corresponds to the longitudinal axis of the hand tool 100, 1000. FIG. 11B shows the tips 160, 260 brought together. FIGS. 11C and 11D show counter-clockwise rotation about Axis 106 and clockwise rotation about Axis 276 and 176. FIG. 11E shows the tips 160, 260 in the scissor configuration.

Other blade configurations are shown in FIGS. 12A-15. The distal portion 170 of the left tip 160 can include a blade 820. The blade 820 can extend from a surface of the left tip 160. The blade 820 can extend to the distal tip 188. The blade 820 can be retracted when the hand tool 100, 1000 functions as forceps. The blade 820 can include the cutting edge 190. The cutting edge 190 can interact with the right section 202 or a corresponding blade 822 to function as scissors. The blade 820 can be the same material as the distal portion 170 of the left tip 160. The blade 820 can be the same material as the left tip 160. The blade 820 can be a different material than the distal portion 170 of the left tip 160. The blade 820 can be a different material than the left tip 160. The blade 820 can be integrally or monolithically formed with the left tip 160. The blade 820 can be a separate component and coupled to the left tip 160.

The distal portion 270 of the right tip 260 can include a blade 822. The blade 822 can extend from a surface of the right tip 260. The blade 822 can extend to the distal tip 288. The blade 822 can be retracted when the hand tool 100, 1000 functions as forceps. The blade 822 can include the cutting edge 290. The cutting edge 290 can interact with the left section 102 or the corresponding blade 820 of the left tip 160 to function as scissors. The blade 822 can be the same material as the distal portion 270 of the right tip 260. The blade 822 can be the same material as the right tip 260. The blade 822 can be a different material than the distal portion 270 of the right tip 260. The blade 822 can be a different material than the left tip 160. The blade 822 can be integrally or monolithically formed with the right tip 260. The blade 822 can be a separate component and coupled to the right tip 260.

In some embodiments, the blade 820 can be retractable within the left tip 160. In some embodiments, the blade 822 can be retractable within the right tip 260. In some embodiments, the blades 820, 822 can be retractable from in a direction from the outside surface to an inside surface. In some embodiments, the blade 820 can be retractable toward the center of the left tip 160. In some embodiments, the blade 822 can be retractable toward the center of the right tip 260. In some embodiments, the blade 820 can pivot relative to left tip 160. In some embodiments, the blade 820 can pivot within the left tip 160 and away from the right tip 260. In some embodiments, the blade 822 can pivot relative to right tip 260. In some embodiments, the blade 822 can pivot within the right tip 260 and away from the left tip 160.

In some embodiments, the blades 820, 822 can be foldable as shown in FIGS. 12A-13B. In some embodiments, the blade 820 can be folded toward a surface of the left tip 160. In some embodiments, the blade 822 can be folded toward a surface of the right tip 260. In some embodiments, the blades 820, 822 are simultaneously retracted. In some embodiments, the blades 820, 822 are independently retracted. In some embodiments, the blades 820, 822 can be retracted in the probe configuration. In some embodiments, the blades 820, 822 can be retracted in the forceps configuration.

In some embodiments, the blades 820, 822 are simultaneously advanced. In some embodiments, the blades 820, 822 are independently advanced. In some embodiments, the blades 820, 822 can be advanced in the scissors configuration.

The two tips 160, 260 of the hand tool 100, 1000 have been described herein. The distal portion 170 of the left tip 160 can include a longitudinally extending portion 182. The longitudinally extending portion 182 can be a portion of a cylinder. The longitudinally extending portion 182 can be semi-circular as shown. The distal portion 270 of the right tip 260 can include a longitudinally extending portion 282. The longitudinally extending portion 282 can be a portion of a cylinder. The longitudinally extending portion 282 can be semi-circular as shown.

The cross-sectional shape can take any form. In some embodiments, the cross-section of the tip is semi-circular. FIGS. 12A-15 and 23A-23B show embodiments of various cross-sectional shapes. In some embodiments, the cross-section of the left tip 160 can be a mirror image of the cross-section of the right tip 260. In some embodiments, the cross-section of the left tip 160 can be the same or substantially the same as the cross-section of the right tip 260.

The cross-section of the tips 160, 260 can be cylindrical or substantially circular. The cross-section of the tips 160, 260 can form any closed shaped (e.g., polygon, triangle, square, rectangle, ellipse, circle, etc.). The cross-section of the tips 160, 260 can include a cutting edge 190, 290. The cutting edge 190, 290 can be a raised edge. The cutting edge 190, 290 can form a discontinuity in the cross-section of the tips 160, 260. The cutting edge 190, 290 can be a ridge. The cutting edge 190, 290 can extend along a portion of the tip 160, 260.

The cross-sectional shape can vary along the length of the tip. In some embodiments, the longitudinally extending portions 182, 282 have the same shape along the length of the longitudinally extending portions 182, 282. In some embodiments, the same shape increases in cross-sectional area along the length of the longitudinally extending portions 182, 282. In some embodiments, the longitudinally extending portions 182, 282 have two or more cross-sectional shapes along the length of the longitudinally extending portions 182, 282. In some embodiments, the cross-section can be a combination of shapes. In some embodiments, the cross-section can be a combination of a circle with one or more additional shapes. In some embodiments, the cross-section of each tip 160, 260 is in the form of a droplet, see also FIGS. 23A-23B. In some embodiments, the cross-section of each tip 160, 260 is in the form of an airfoil. In some embodiments, the cross-section of each tip 160, 260 has rotational symmetry about an axis through the cutting edge 190, 290. In some embodiments, the cross-section of each tip 160, 260 has a rounded or curved section. In some embodiments, the cross-section of each tip 160, 260 has a pointed section. Two such embodiments are disclosed in FIGS. 23A-23B.

In some embodiments, the hand tool 100, 1000 can include one or more springs. In the embodiment described herein, the hand tool 100, 1000 can include the left spring 124 and the right spring 224. In some embodiments, the hand tool 100, 1000 includes one or more springs. Other embodiments are contemplated (one spring, two springs, three springs, four springs, five springs, etc.). One or more springs can be coupled to the left handle 132. One or more springs can be coupled to the right handle 232. One or more springs can bias the handles 132, 232 toward each other. One or more springs can bias the left handle 132 toward the right handle 232. One or more springs can bias the right handle 232 toward the left handle 132.

One or more springs can bias the left handle 132 toward a neutral position. One or more springs can bias the right handle 232 toward a neutral position In some embodiments, the neutral position can be associated with the forceps configuration, the scissor configuration, the probe configuration or another or intermediate position. In some embodiments, the neutral position can be unassociated with the configurations described herein.

In some embodiments, the springs bias the hand tool toward the forceps configuration. In some embodiments, the springs bias the hand tool toward the scissor configuration. In some embodiments, the springs bias the hand tool toward the probe configuration.

In some embodiments, the hand tool 100, 1000 has a spring lockout. The spring lockout can stiffen the spring in one or more configurations. In some embodiments, the spring lockout can lock out part of the spring system to stiffen the hand tool 100, 1000. In some embodiments, the hand tool 100, 1000 can lockout part of one or more springs to stiffen in forceps.

Referring back to FIGS. 2A-4, the hand tool 100, 1000 can transition between the forceps configuration and the scissors configuration. The forceps configuration is shown in FIG. 2A and the scissors configuration is shown in FIG. 4. The intermediate configuration is shown in FIG. 3. The hand tool 100, 1000 permits the switching between the forceps configuration and the scissors configuration. The hand tool 100, 1000 can transition between these configurations by rotation of the tips 160, 260 of the hand tool 100, 1000, as described herein. The tips 160, 260 are rotated between the forceps configuration shown in FIG. 2A and the scissors configuration shown in FIG. 4. The tips can be brought together in the intermediate configuration as shown in FIG. 3 during the transition between the forceps configuration and the scissors configuration.

The hand tool 100, 1000 can include a probe configuration as shown in greater detail in FIGS. 16-19. In some embodiments, the hand tool 100, 1000 functions as a unipolar probe in the probe configuration. In some embodiments, the hand tool 100, 1000 functions as a bipolar probe in the probe configuration. In some embodiments, the hand tool 100, 1000 functions as a multipolar probe in the probe configuration. The hand tool 100, 1000 can include the left handle 132 and the right handle 232. The hand tool 100, 1000 can include the left tip 160 and the right tip 206. The left handle 132 and the right handle 232 can retain the left tip 160 and the right tip 260 as described herein. The left handle 132 and the right handle 232 can be brought together in order to transition the hand tool 100, 1000 between the forceps configuration and the scissors configuration as described herein.

In some embodiments, the probe configuration is the intermediate configuration between the scissors configuration and the forceps configuration. FIG. 3 shows as example of the hand tool 100, 1000 in the intermediate position, according to some embodiments. FIG. 3 shows as example of the hand tool 100 in the a probe configuration. In some embodiments, in the probe configuration, the handles 132,

232 are moved toward each other. In some embodiments, the left handle 132 is moved toward the right handle 232. In some embodiments, the right handle 232 is moved toward the left handle 132. In some embodiments, the user applies a force to overcome the biasing force of the springs 124, 224. In some embodiments, the internal surface of the handles 132, 232 can abut. In other embodiments, the internal surface of the handles 132, 232 are near each other but do not abut in the probe configuration. In some embodiments, the left tip 160 and the right tip 260 can be brought together. In some embodiments, the tips 160, 260 can abut. In other embodiments, the left tip 160 and the right tip 260 are near each other but do not abut in the probe configuration. The internal flat surfaces 184, 284 can abut. In some embodiments, the left tip axis 158 and the right tip axis 258 can align in the probe configuration. In other embodiments, the left tip axis 158 and the right tip axis 258 do not align in the probe configuration. In some embodiments, the protrusion 294 can engage the recess 194 in the probe configuration. In some embodiments, the probe configuration is a low-profile configuration. In some embodiments, one or more components of the left section 102 are brought together or abuts one more components of the right section 202.

Figure 17:
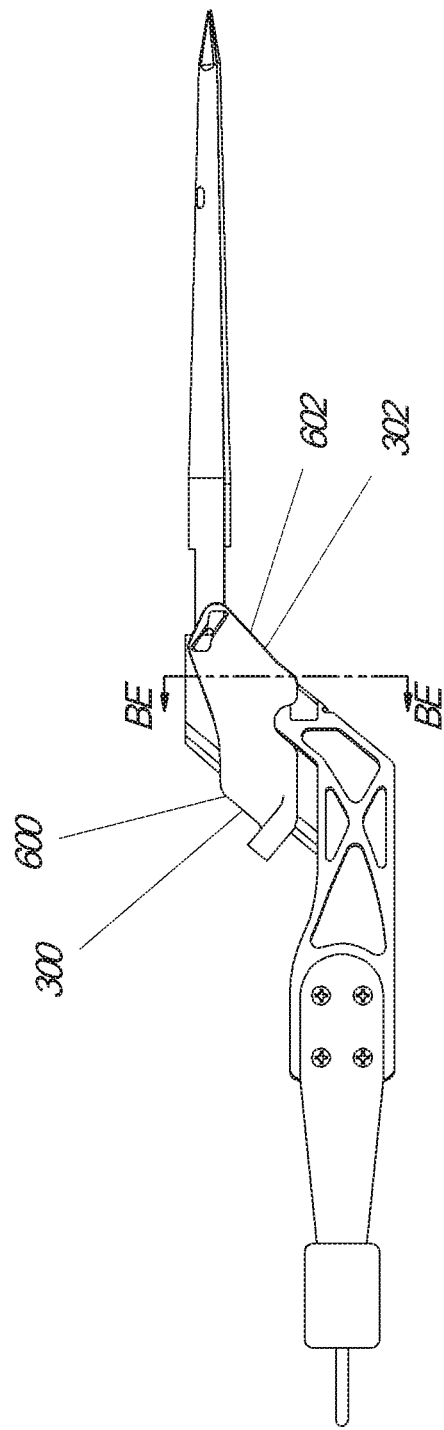
Figure 18:
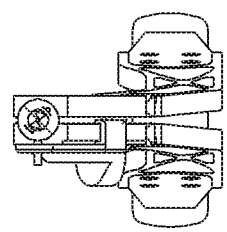
Figure 19:
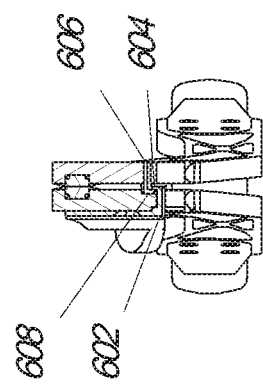

In some embodiments, the hand tool 100, 1000 includes a mechanism 600. The mechanism 600 is shown in FIGS. 17-19. The mechanism 600 can be a slide 602 or other component capable of performing the function described herein. The hand tool 100, 1000 can include a mechanism 600 that enables the user to transition between the forceps configuration and the scissors configuration. The handles 132, 232 can be brought together to allow translation of the slide 602. Translation of the slide 602 transitions the tool between the various configurations. In some embodiments, translation of the slide 602 can provide a lockout, preventing the two sections 102, 202 from separating. In some embodiments, the lockout limits the tips 160, 260 from separating in the probe configuration. In some embodiments, the lockout limits the handles 132, 232 from separating in the probe configuration. In some embodiments, the lockout can prevent the two sections 102, 202 from separating over a portion of the translational motion of the slide.

The mechanism 600 can have any of the features described herein with respect to mechanism 300. The slide 602 can be made to have a portion which extends to the medial side of the handle 132, 232 to which it is coupled. In the illustrated embodiment, the slide 602 is coupled to the right handle 232. The medial portion of the slide 602 can have a slide latch 604. The slide latch 604 can be a ridge that acts as a latch. The handle opposing the slide 602 can be fitted with a peg 606. In the illustrated embodiment, the handle opposing the slide 602 is the left handle 132. The peg 606 can be coupled to the left handle 132 to protrude medially. The peg 606 can have a portion 608 that protrudes. The protruding portion 608 of the peg 606 can be made to interact with the slide latch 604 of the slide 602. The slide 602 and the peg 606 can be coupled to the hand tool so that the peg 606 is free from the slide latch 604 at the extremes of translation of the slide 602. The extremes of translations of the slide 602 can be 100% or less of the total motion of the slide 602 from either direction. In some embodiments, one extreme of translations correspond to the scissor configuration. In some embodiments, one extreme of translations corresponds to the forceps configuration. In some embodiments, the opposite extremes of translations correspond to the scissor configuration and the forceps configuration. In some embodiments, the translation of the slide between the extremes of translations corresponds to the intermediate configuration and/or the probe configuration.

The slide latch 604 can be made to interact with the protruding portion 608 of the peg 606 when the slide 602 is not in a translational extreme. The interaction of the slide latch 604 on one handle with the protruding portion 608 of the peg 606 of the opposing handle can have the effect of retaining the sections 102, 202 together in probe configuration. The interaction of the slide latch 604 with the protruding portion 608 of the peg 606 can limit the handles 132, 232 from separating in the probe configuration. The interaction of the slide latch 604 with the protruding portion 608 of the peg 606 can limit the tips 160, 260 from separating in the probe configuration. In other embodiments, the slide latch 604 can be made to latch in either of a translational extreme. In other embodiments, secondary mechanism (not shown) can be made to latch in either of a translational extreme, for instance the translation extreme corresponding to the scissor configuration. The secondary mechanism can limit the handles 132, 232 from separating in the scissor configuration. The secondary mechanism can limit the tips 160, 260 from separating in the scissor configuration.

The interaction of the slide latch 604 and the protruding portion 608 of the peg 606 can prevent the handles 132, 232 from being allowed to separate unless the slide 602 is in an extreme of translation. The interaction of the slide latch 604 and the protruding portion 608 of the peg 606 can prevent the handles 132, 232 from being allowed to separate unless the hand tool 100, 1000 is in the scissor configuration. The interaction of the slide latch 604 and protruding portion 608 of the peg 606 can prevent the handles 132, 232 from being allowed to separate unless the hand tool 100, 1000 is in the forceps configuration. Placing the slide 602 in either extreme of translation can disengage the slide latch 604 from the protruding portion 608 of the peg 606. Placing the slide 602 in either translational extreme can allow the halves of the hand tool 100, 1000 to separate allowing use of either the scissors or forceps.

In some embodiments, the hand tool 100, 1000 has an intermediate position lockout. The intermediate position lockout can include the mechanism 600 or another mechanism configured to maintain the intermediate position or probe position. The mechanism 600 of the hand tool 100, 1000 can operate to lockout handles 132, 232 from separating unless completely in either the scissors configuration or the forceps configuration. The hand tool 100, 1000 operates to lockout handles 132, 232 in the intermediate configuration or probe configuration. In some embodiments, the hand tool 100, 1000 in the intermediate configuration acts as a probe. The hand tool 100, 1000 in the probe configuration can conduct an electrical signal or current. The hand tool 100, 1000 in the probe configuration can allow monopolar cutting, cauterization, and fulguration. The hand tool 100, 1000 in the probe configuration can allow hardware detection. The hand tool 100, 1000 in the probe configuration can allow nerve, muscle, and tissue stimulation. The hand tool 100, 1000 in the probe configuration can allow nerve, muscle, tissue, and implant detection. The hand tool 100, 1000 in the scissors configuration can allow nerve, muscle, and tissue stimulation. The hand tool 100, 1000 in the scissors configuration can allow nerve, muscle, and tissue detection. The hand tool 100, 1000 in the forceps configuration can allow nerve, muscle, and tissue stimulation. The hand tool 100, 1000 in the forceps configuration can allow nerve, muscle, and tissue detection. The surgical hand tool can include electrodes as described herein. The left tip 160 can include an electrode 192. The right tip 260 can include an electrode 292. In the probe configuration, one of the electrodes 192, 292 or another electrode of the hand tool 100, 1000 can be supplied with electrical current. One of the tips 160, 260 can include electrode for monopolar electrosurgery. The electrode can be located on the longitudinally extending portion 182, 282. The electrode can be located on an external surface of the tips 160, 260. The electrode can be located on an internal surface of the tips 160, 260, for instance the flat surfaces 184, 284. The electrode can be configured for cauterization, hemostasis, and tissue dissection.

The method can include one or more of the following steps. The method can include placing the slide 602 in an intermediate position. In some embodiments, the intermediate position of the slide can allow the two handles 132, 232 of the hand tool 100, 1000 to remain in proximity. In some embodiments, the intermediate position of the slide can allow the two tips 160, 260 of the hand tool 100, 1000 to remain in proximity. In some embodiments, the intermediate position of the slide corresponds to the intermediate position of the hand tool 100, 1000 or the probe configuration.

The method can include placing the slide 602 in a first extreme translation position. In some embodiments, the first extreme translation position of the slide can allow the two handles 132, 232 of the hand tool 100, 1000 to remain in proximity. In some embodiments, the first extreme translation position of the slide can allow the two tips 160, 260 of the hand tool 100, 1000 to remain in proximity. In some embodiments, the first extreme translation position corresponds to the scissor configuration.

The method can include placing the slide 602 in a second extreme translation position. In some embodiments, the second extreme translation position of the slide can allow the two handles 132, 232 of the hand tool 100, 1000 to separate. In some embodiments, the second extreme translation position of the slide can allow the two tips 160, 260 of the hand tool 100, 1000 to separate. In some embodiments, the first extreme translation position corresponds to the forceps configuration. The first extreme translation position can be opposite to the second extreme translation position along the translational length of the slide 602. The intermediate position can be between the first and the second extreme translation positions.

In some embodiments, while in the unipolar probe configuration, the hand tool 100, 1000 can be used as a probe. In some embodiments, the device can be used for probe dissection. In some embodiments, the device can be used for blunt dissection. In some embodiments, while in the unipolar probe configuration, electrical energy can be applied to the hand tool 100, 1000 to facilitate unipolar cauterization, ablation, hardware detection, tissue stimulation (nerve, muscle, etc.) or other functions. In some embodiments, the while in any configuration, the device may transmit energy intended for tissue manipulation.

Figure 20:
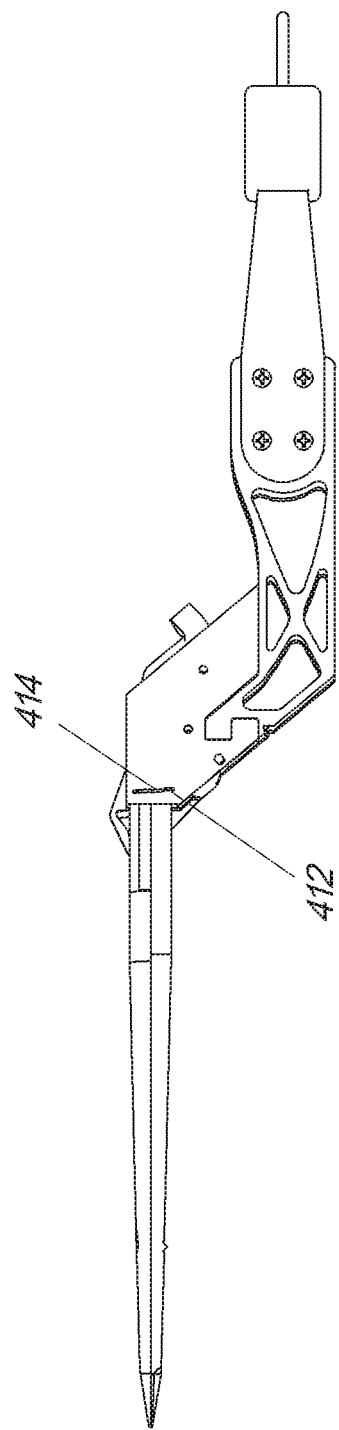
Figure 21:
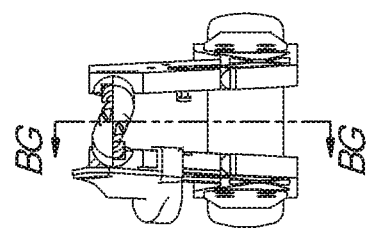
Figure 23A:
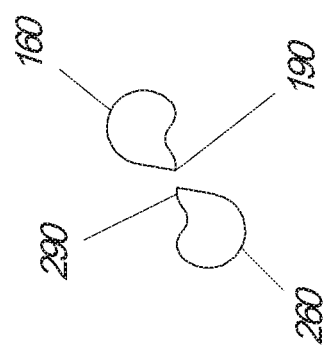
Figure 23B:
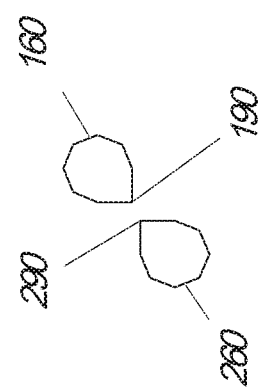

In some embodiments, the hand tool 100, 1000 includes a scissor axis lock by tip translation shown in FIGS. 20-22. Referring back to FIGS. 9A-9D, the sleeve 400 can function to hold the tips 160, 260 together in the scissors configuration. Other mechanisms are contemplated which allow for positive locking of the tips 160,260 in the scissors configuration.

Referring now to FIGS. 20-22, in some embodiments, either or both of the tips can contain a pin 412 on the proximal portion protruding from the external surface. In some embodiments, at least one handle 132, 232 can contain a slot/recess 414 to receive the pin 412. The slot 414 can be configured to guide the pin 412. As one example, one of the tips 160, 260 can have a protrusion 294 and the other tip can have a recess 194. In the illustrated embodiments, the left tip 160 can have the recess 194 and the right tip 260 can have the protrusion 294. The guiding slot 414 defines translation of the tip 160 along the longitudinal axis relative to the other tip 260 and to the handles 132, 232. The tip 160 can translate distally or proximally while it rotates. This translation locks or releases the pin 294 and recess 194 in FIG. 22. Either of the tips and/or the handles can be configured with the guiding slot or pin such that one is received within the other. Other such embodiments can include translation of a portion of the tip 160, 260.

The slot 414 can be configured so that rotation of the tip about the longitudinal axis produces translation of one tip relative to the handle. The slot 414 can be configured to direct translation of one tip relative to the handle. The recess 194 can be configured such that translation of the pin 412 within the guiding slot 414 directs translation of the tip(s) 160, 260 along and/or perpendicular to the longitudinal axis 106 with respect to each other and/or the handles 132, 232. The slot can be configured so that when the handles are brought together, at least one tip shears past another tip. As one example, the protrusion 294 and the recess 194 can provide an axis 198 upon which the tips 160, 260 can pivot relative to each other. The protrusion 294 can engage the recess 194 when the hand tool 100, 1000 is in the scissor configuration. The protrusion 294 can engage the recess 194 when the hand tool 100, 1000 is in the intermediate configuration or probe.

Other means of causing translation of one tip relative to the handle or other tip are contemplated. Other means can include a screw, spiral, gear, cable, motor, etc. In some embodiments, all, any or multiple components are made to translate. The slot 414 can be configured to allow all or any portion of the tips 160, 260 to translate relative to the handles 132, 232.

In some embodiments, the scissor axis pin can contain a mating configuration. The tip which receives the scissor axis pin can contain a complimentary recess. For instance, the protrusion 294 can include a recess 418, protrusion or other mating configuration (FIG. 22). The tip 160 that does not include the pin 294 can include a recess 194 (FIG. 22). Translation of one tip relative to the other can engage the respective mating configurations of the protrusion 294 and the opposing tip 160 to facilitate positive retention of the two tips 160, 260 in proximity. The mating configuration can take any form.

Figure 24:
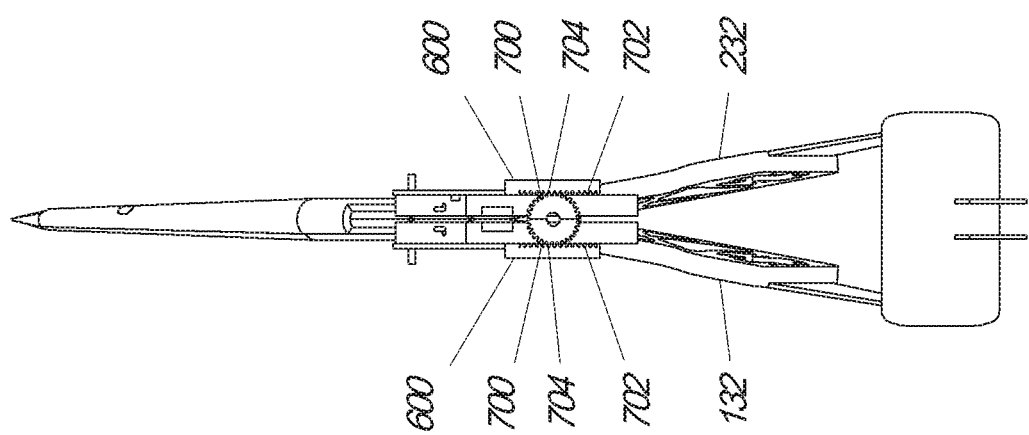
Figure 25:
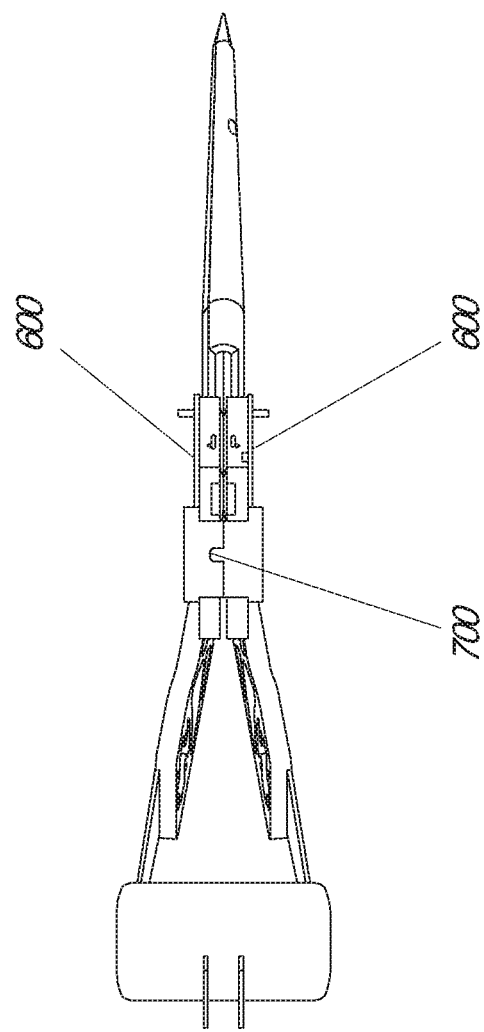

FIGS. 24-25 shows an ambidextrous mechanism or actuating mechanism. In some embodiments, the hand tool 100, 1000 can be made for either right or left handed use. In some embodiments, the hand tool 100, 1000 can be made for ambidextrous use. In some embodiments, the left handle 132 can be moved toward the right handle 232 to transition the hand tool 100, 1000. In some embodiments, the right handle 232 can be moved toward the left handle 132 to transition the hand tool 100, 1000. In some embodiments, the user can determine whether the left handle 132 is configured to move relative to the right handle 232 or whether the right handle 232 is configured to move relative to the left handle. In some embodiments, the handles 132, 232 are brought toward, for instance, by moving each handle 132, 232 substantially equally. In some embodiments, the hand tool 100, 1000 can include features to make the hand tool ambidextrous.

In some embodiments, the hand tool 100, 1000 includes one or more actuating mechanism 700 to replicate the user's movement. In some embodiments, the actuating mechanism 700 replicates movements performed on left section 102 with corresponding movements of the right section 202. In some embodiments, the actuating mechanism 700 replicates movements performed on right section 202 with corresponding movements of the left section 102. The actuating mechanism 700 can include gears, pins, springs, slides etc. which facilitate the replication of movement. The actuating mechanism 700 can include gears, cables, motors, magnets or any other means of transmitting force. The actuating mechanism 700 can cause corresponding movement of both handles 132, 232 if only handle 132, 232 is moved. The actuating mechanism 700 can cause corresponding movement of slides 300, 600 of both handles 132, 232 if only one slide 300, 600 is moved. The actuating mechanism 700 can cause corresponding movement of both tips 160, 260 if only tip 160, 260 is moved. The actuating mechanism 700 can duplicate the movement of components of one side of the hand tool 100, 1000 with movements of components of the opposing side of the hand tool.

The hand tool 100, 1000 can be fit with an actuating mechanism 700 on both sides. In some embodiments, the handle tool includes one or more slides 300, 600 on each handle 132, 232. The actuating mechanisms 700 can interact with two slides, for instance two slides 300 or two slides 600. The two slides can be positioned on the handles 132, 232. The actuating mechanisms 700 can be made such that they interact upon transitioning the hand tool 100, 1000 between functional configurations. The actuating mechanisms 700 can be made to allow separation of the handles and mechanisms. The actuating mechanisms 700 can be made to work in similar or opposing directions. The actuating mechanisms 700 can interact by any means to accomplish transitioning of the device between functional configurations.

In some embodiments, the pair of slides coupled to the handles 132, 232 can have additional features. The pair of slides 300 or the pair of slides 600 can include a cog surface 702 on their respective medial sides. Each of the superior portions of the handles 132, 232 can include a semicircular gear 704. The gears 704 can be any shape including any portion of a circle, square, triangle or any combination. The gears 704 can be fit to the respective handle 132, 232 such that the gears 704 interact with the cog surface 702 of the slides 300, 600. The gears 704 can be coupled to their respective handles 132, 232 such that the two semi-circular gears 704 interact with each other when the handles 132, 232 are brought together. Other configurations of the actuating mechanisms 700 are contemplated.

In some embodiments, translation of either slide 300, 600 can transition the hand tool 100, 1000 between functional configurations. Translation of either slide 300, 600 can effect translation of the opposing slide 300, 600. Other embodiments are considered to transfer force and movement from the actuating mechanism of one side to the other. Other embodiments can include one or any number or combination of gears, cables, motors, etc. In some embodiments, the actuating mechanisms can interact directly with each other.

The two tips 160, 260 of the hand tool 100, 1000 are described herein. In some embodiments, the tips 160, 260 can protrude from the handles 132, 232. In some embodiments, the tips 160, 260 can be made as a single part. The single part can extend from the handle 132, 232 to the cutting edge. The single part can extend from the handle 132, 232 to the electrode surface 192, 292.

Figure 26:
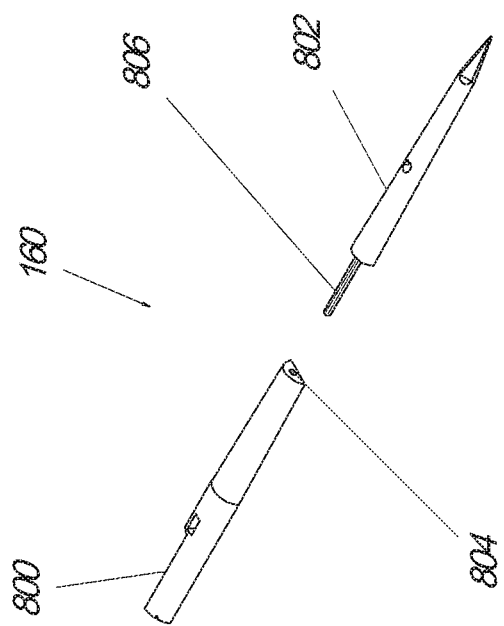

In some embodiments, each of the tips 160, 260 can be formed of multiple parts (e.g., two, three, four, five, six, seven, etc.). FIG. 26 shows an embodiment of the left tip 160. The right tip 260 can have similar features as shown in FIG. 26. The left tip 160 can include a proximal portion 800 and a distal portion 802. In some embodiments, the proximal portion 800 of the tip 160 can interact with the handle 132 (not shown). The proximal portion 800 of the tip 160 can include a mating feature 804. In the illustrated embodiment, the mating feature 804 is a receiving portion including a recess. The distal portion 802 of the tip 160 can include a mating feature 806. In the illustrated embodiment, the mating feature 806 is a projection. Other mating features 804, 806 are contemplated including recess, protrusion, ridge, latch, peg, slot, etc. The proximal end of the distal portion 802 of the tip can be made to interact with the distal end of the proximal portion 800. In the illustrated embodiment, the projection of the distal portion 802 of the tip 160 can be made to fit within the recess of the proximal portion 800. The proximal portion 800 can be made to interact in any way to retain the distal portion 802.

In some embodiments, the distal portion 802 of the tip 160 can be a separate replaceable component. The replaceable component can have a cutting edge 190 on the distal portion. The replaceable component can have an electrode 192 surface on the distal portion. The proximal portion 800 can be made to interact in any way to retain the replaceable component. This can include a recess, protrusion, ridge, latch, or any other mechanism for retaining the replaceable component to the proximal portion 800 of the tip 160. The replaceable component of the tip 160 can be made for one-time use. The replaceable component of the tip 160 can be made for multiple uses. The replaceable component of the tip 160 can be made to any length. The replaceable component can be made to any shape including straight, curved, round, flat, upward projecting, downward projecting, etc.

In some embodiments, a hand tool is disclosed. The hand tool can be in the general form of forceps or microscissors. In some embodiments, two portions being brought towards each other effectuates two or more other portions to come together. In some embodiments, two portions being brought towards each other effectuates two or more other portions to come together by translation. In some embodiments, two portions being brought towards each other effectuates two or more other portions to come together by rotation. In some embodiments, two portions being brought towards each other effectuates two or more other portions to come together by any other movement. In some embodiments, two portions being brought towards each other effectuates two or more other portions to come together that can be used in two or more mechanical functions. In some embodiments, the mechanical function includes grasping. In some embodiments, the mechanical function includes compression forceps. In some embodiments, the mechanical function includes cutting shears. In some embodiments, the two portions being brought together are perpendicular or generally perpendicular to the longitudinal axis. In some embodiments, the two portions being brought together are substantially not aligned to the longitudinal axis. In some embodiments, the two portions being brought together are skewed relative to the longitudinal axis. In some embodiments, the motion of bringing together is generally not aligned with the axis of the working portion. In some embodiments, the motion of bringing together is generally not aligned with one or more of the tips.

In some embodiments, two portions being brought towards each other effectuates two or more other portions to be brought apart. In some embodiments, two portions being brought towards each other effectuates two or more other portions to be brought apart by translation. In some embodiments, two portions being brought towards each other effectuates two or more other portions to be brought apart by rotation. In some embodiments, two portions being brought towards each other effectuates two or more other portions to be brought apart by any other movement. In some embodiments, two portions being brought towards each other effectuates two or more other portions to be brought apart that can be used in two or more mechanical functions.

One advantage is that the hand tool can perform at least two distinct mechanical functions. One advantage is that the hand tool can perform three distinct mechanical functions. The hand tool can operate as scissors. The hand tool can operate as forceps. The hand tool can operate as a probe. The hand tool can be used for cutting. The hand tool can be used for distraction. The hand tool can be used for probing. One advantage is that the hand tool can be in the form of forceps or microscissors and perform two distinct mechanical functions. One advantage is that the hand tool can perform the distinct mechanical functions of grasping or compression. One advantage is that the hand tool can perform the distinct mechanical functions of distraction. One advantage is that the hand tool can perform the distinct mechanical functions of shearing or cutting. One advantage is that the hand tool can perform the distinct mechanical functions of probing, sensing, applying energy, or cauterization. One advantage is that the hand tool can perform the distinct mechanical functions regardless of how that action is achieved (by rotating, switching, elevating, etc.).

Figure 27:
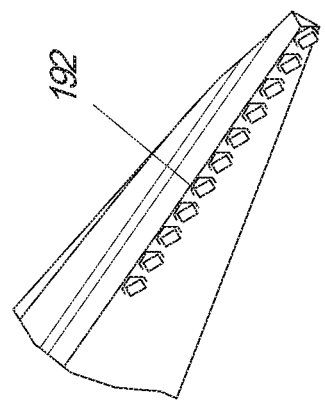
FIGS. 27-28 show embodiments of an electrode.
Figure 28:
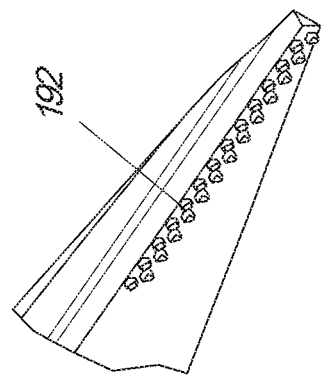
Figure 29:
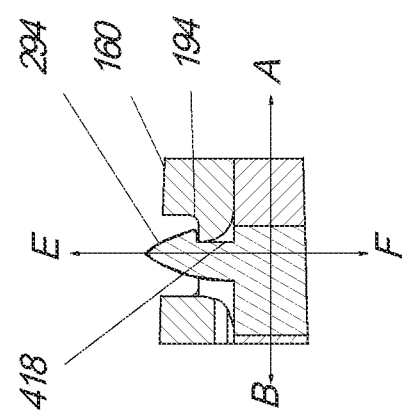
FIGS. 29-30 show embodiments of a recess and a protrusion.
Figure 30:
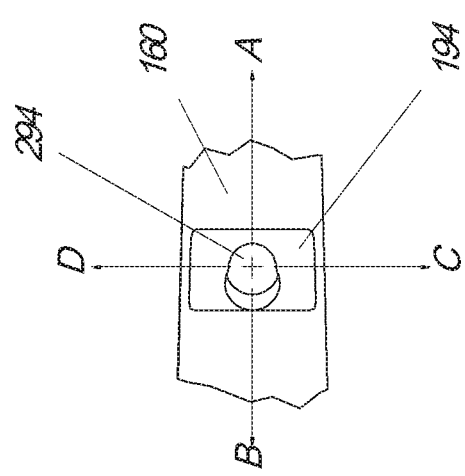
Figure 32B:
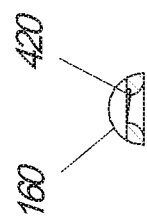
Figure 32A:
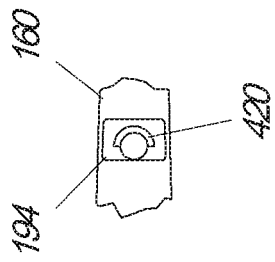
Figure 34:
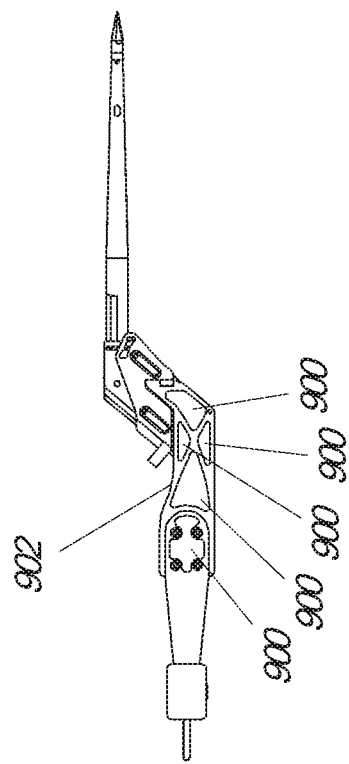
FIGS. 34-39 show an embodiment of a hand tool.
Figure 35:
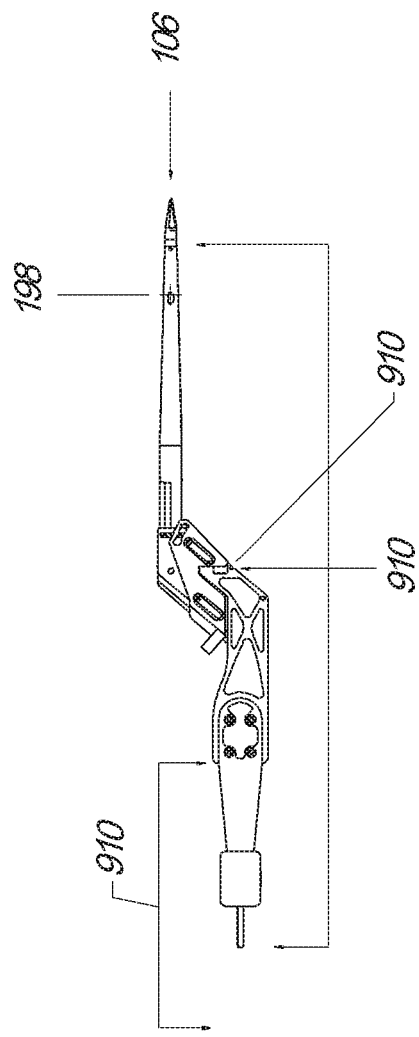
Figure 36:
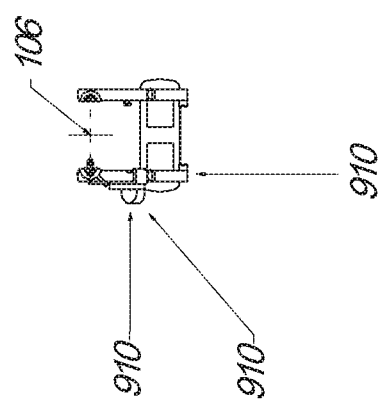
Figure 37:
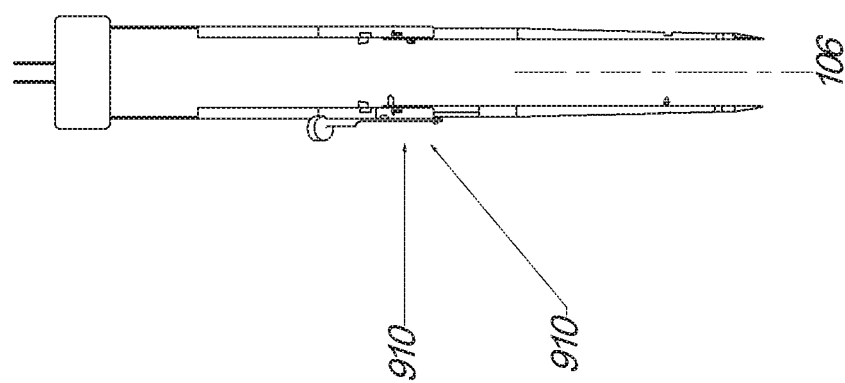
Figure 38:
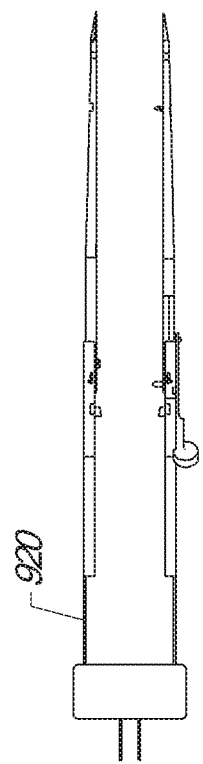
Figure 39:
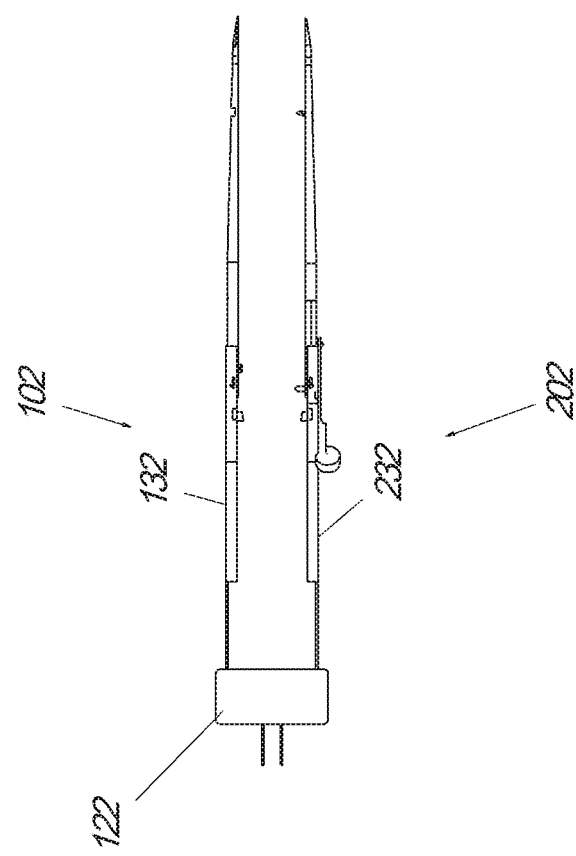
Figure 40:
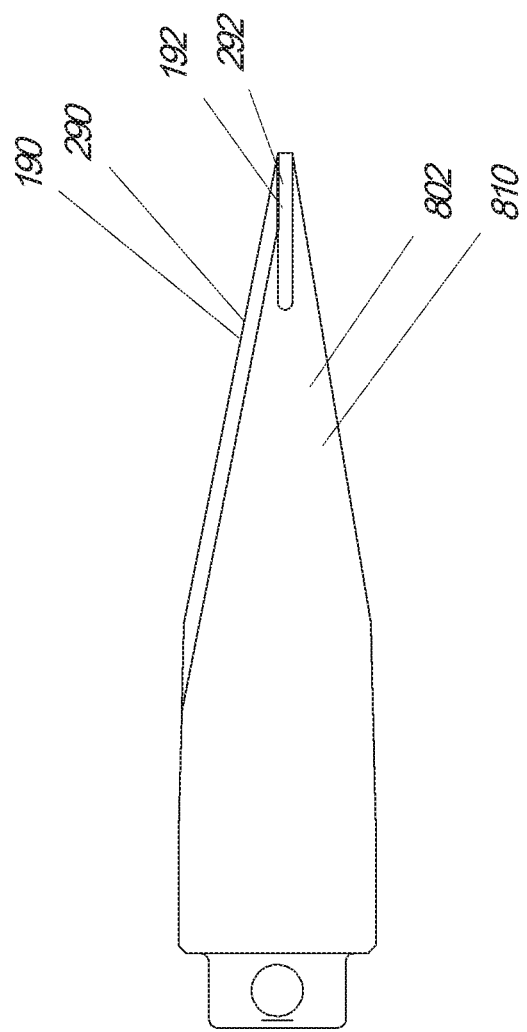
FIG. 40 shows an embodiment of a tip.

FIGS. 27 and 28 show embodiments of an electrode 192, 292. In some embodiments, one or more electrodes 192, 292 can have interrupted surface areas. In some embodiments, one or more electrodes 192, 292 can have multiple surface areas. In some embodiments, one or more electrodes 192, 292 can have multiple surface areas as the anode. In some embodiments, one or more electrodes 192, 292 can have multiple surface areas as the cathode. In some embodiments, an electrode 192, 292 can have a combined or individual conductive surface area less than 0.005 square inches, less than 0.004 square inches, less than 0.003 square inches, less than 0.002 square inches, less than 0.001 square inches, less than 0.0005 square inches, less than 0.0002 square inches, less than 0.0001 square inches, less than 0.00005 square inches, less than 0.00001 square inches, between 0.00001 and 0.01 square inches, between 0.0001 and 0.01 square inches, etc.

Referring back to FIGS. 20-22, the hand tool 100, 1000 includes a scissor axis lock by tip translation. FIGS. 29-33 show an embodiment of a mechanism to allow for positive locking of the tips 160, 260 in the scissors configuration. One or more recesses about the scissor axis pivot can guide tip separation. One or more recesses about the scissor axis pivot can limit tip separation. One or more protrusions about the scissor axis pivot can guide tip separation. One or more protrusions about the scissor axis pivot can limit tip separation. The one or more recesses and/or protrusions can guide and/or limit tip separation in the direction of E-F. Translation along the longitudinal axis can engage the respective one or more recesses of the scissor axis pivot and tip. Translation along the longitudinal axis can engage the one or more respective protrusion of the scissor axis pivot and tip or portion of tip.

Other means of retaining the tips in proximity are contemplated. In one such embodiment a magnet 416 can be disposed within the body of either or both of the tips 160, 260. FIG. 31 shows one configuration of the magnets 416, but other configurations are contemplated. The one or more magnets 416 can be positioned such that an attractive or repulsive force between the tips is achieved. The one or more magnets 416 can be placed at any position within the tips 160, 260. The one or more magnets can increase the force required to separate tips. The one or more magnets can decrease the force required to separate tips. The one or more magnets can be placed anywhere including the distal tip, the proximal tip, the handle, etc.

FIGS. 29-33 show an embodiment of a protrusion and a recess. A tip 160 can have a recess 194 to engage the protrusion 294. The recess 194 can be formed to consist of a ramp, taper, or spiral 420 to guide engagement of the protrusion 294. The ramp 420 can be configured such that rotation about the axis 198 can produce translation of the tips toward or away from each other. The ramp 420 and recess 194 can be configured such that rotation about the axis 198 can produce translation of one tip relative to the other. The recess 194 can include a ramp. The recess 194 can include a taper. The recess 194 can include a guide. The protrusion 294 can include a ramp. The protrusion 294 can include a taper. The protrusion 294 can include a guide. The ramp, taper, guide of the recess 194 can retain medial surface of tips in proximity. The ramp, taper, guide of the protrusion 294 can retain medial surface of tips in proximity. The ramp, taper, guide of the recess 194 can maintain force on cutting edge. The ramp, taper, guide of the protrusion 294 can maintain force on cutting edge. The ramp, taper, guide of the recess 194 can produce translation on rotation about scissor axis 198. The ramp, taper, guide of the protrusion 294 can produce translation on rotation about scissor axis 198. The ramp, taper, guide of the recess 194 can produce translation along the direction of E-F on rotation about scissor axis. The ramp, taper, guide of the protrusion 294 can produce translation along the direction of E-F on rotation about scissor axis.

In some embodiments, the hand tool can enable guiding or limiting of translation of one tip relative to the hand tool. In some embodiments, the hand tool can enable guiding or limiting of translation of the other tip along a relative direction. In some embodiments, the hand tool can enable guiding or limiting of translation of the other tip along a relative direction such as along A-B. In some embodiments, the hand tool can enable guiding or limiting of translation of the other tip along a relative direction such as along the longitudinal axis. In another embodiment, the hand tool can enable guiding or limiting of any portion of the device or tip relative to any other portion of the device or tip.

In some embodiments, the hand tool can enable guiding or directing of movement or translation of the other tip along a direction perpendicular to the longitudinal or central axis. In some embodiments, the hand tool can limit movement or translation of the other tip along direction perpendicular to the longitudinal or central axis. In some embodiments, the hand tool can enable guiding or directing of movement or translation of the other tip along direction perpendicular to the longitudinal or central axis such as C-D or E-F. In some embodiments, the hand tool can limit movement or translation of the other tip along direction perpendicular to the longitudinal or central axis such as C-D or E-F. In some embodiments, the hand tool can enable guiding or directing of movement or translation of the other tip along direction substantially parallel to the longitudinal or central axis. In some embodiments, the hand tool can limit movement or translation of the other tip along direction substantially parallel to the longitudinal or central axis. In some embodiments, the hand tool can enable guiding or directing of movement or translation of the other tip along direction substantially oblique to the longitudinal or central axis. In some embodiments, the hand tool can limit movement or translation of the other tip along direction substantially oblique to the longitudinal or central axis. In some embodiments, translation/rotation in at least one direction limits translation/rotation in at least one degree of freedom. In some embodiments, translation in at least one direction limits movement in at least another direction. In some embodiments, rotation in at least one direction limits movement in at least another direction. In some embodiments, movement in at least one direction limits movement in at least another direction. In some embodiments, translation in at least one degree of freedom limits movement in at least another degree of freedom. In some embodiments, rotation in at least one degree of freedom limits movement in at least another degree of freedom. In some embodiments, movement in at least one degree of freedom limits movement in at least another degree of freedom.

FIG. 33 shows an example of the guiding slot 414. The handle can include a slot, groove, recess or other guiding device. The guiding slot 414 can direct or limit translation along direction of longitudinal or central axis. The guiding slot 414 can be on either of the handles. The guiding slot 414 can be on either of the tips. A guiding slot 414 can be on both handles. A guiding slot 414 can be on both tips.

FIGS. 34-39 show an embodiment of the hand tool. The hand tool can include one or more apertures 900. The hand tool can include multiple apertures 900. The hand tool can include no apertures 900. In some embodiments either handle can include one or more apertures 900. In some embodiments either handle can include no apertures. In some embodiments both handles can include one or more apertures 900. In some embodiments both handles can include no apertures. In some embodiments, the apertures can be formed of any size, area, volume, weight, perimeter or any other dimension. In some embodiments the wall 902 surrounding an aperture can be 0-0.5" thick in any dimension. In some embodiments the wall 902 surrounding an aperture can be 0-0.125" thick in any dimension. In some embodiments, any combination of one or more apertures 900, recesses, or bosses can be incorporated in any size, form or position. In some embodiments, the combination of one or more apertures 900, recesses, or bosses can be for weight reduction. In some embodiments, the combination of one or more apertures 900, recesses, or bosses can be for sectional strength modulation. In some embodiments, the combination of one or more apertures 900, recesses, or bosses can be for grip or for any other purpose.

In some embodiments, the hand tool can include a flexible region or pivot axis distal to the grip. In some embodiments, the hand tool can include a flexible region or pivot axis distal to the proximal end of the device. In some embodiments, the hand tool can include multiple pivot axes or flexible regions. In some embodiments, the hand tool can include a pivot axis proximal to the proximal end of the device. In some embodiments, any axis can be aligned, perpendicular, parallel or at any angle to any other axis Referring now to FIGS. 35-39, an embodiment that allows central flexibility is contemplated. In some embodiments, the central flexible portion can comprise a flexible region or axis 910. In some embodiments, the flexible region can include a pivot axis. In some embodiments, the central flexible region or axis 910 can comprise any portion of the device 100, 1000. In some embodiments, the central flexible region or axis 910 can be allowed over a length of the device 100, 1000. In some embodiments, the central flexible region or axis 910 can be positioned between the proximal 116 and distal 118 ends of the device. In some embodiments, the central flexible region can include all or a portion of the handle(s) 132, 232. In some embodiments, the central flexible region can include all or a portion of the tip(s) 160, 260. In some embodiments, the central flexible region can include all or a portion of any or all parts of the device.

In some embodiments, the central flexible region can include a pivot. The pivot can be made to allow flexibility between portions of the handle(s) 132, 232. In some embodiments, the central flexible region can have a neutral position. In some embodiments, the central flexible region can be made to allow a distal portion of the device to move with respect to a proximal portion of the device. In some embodiments, the central flexible region can allow a proximal portion of the handle to move with respect a distal portion of the handle.

In some embodiments, a flexible region or axis 910 can be comprised of aperture(s) 900, recess(es) 920 or any other shape. Any cross sectional shape can be used to achieve desired flexibility, stiffness, shape, weight, feel, and/or any other property.

In some embodiments, the hand tool can include one more components that are integrated. In some embodiments, the hand tool can be include one more components that are monolithically formed. In some embodiments, the hand tool can include one more components that are injection molded. In some embodiments, the hand tool can include one more components that are stamped. In some embodiments, the hand tool can include the rear assembly of connector, spring, and/or handle as one part or multiple parts.

FIG. 41 shows an embodiment of a tip. In some embodiments, electrical and/or dielectric insulation 810 of tip can be limited to distal portion 802. In some embodiments, electrical and/or dielectric insulation 810 of tip can be limited to distal portion 802 excluding surface electrode. In some embodiments, electrical and/or dielectric insulation 810 of tip does not cover the entire device. In some embodiments, electrical and/or dielectric insulation 810 of tip can include the cutting edge. In some embodiments, electrical and/or dielectric insulation 810 of tip can exclude the cutting edge. In some embodiments, two or more of the electrode surface, distal tip and cutting edge can be monolithically formed. In some embodiments, the electrode surface, distal tip and cutting edge can all be monolithically formed. In some embodiments, two or more of the electrode surface, distal tip and cutting edge can be separate pieces. In some embodiments, the electrode surface, distal tip and cutting edge can all be separate pieces. The electrode surface can be coated. The electrode surface can be plated. The electrode surface can be uncoated. The scissor edge can be coated. The scissor edge can be plated. The scissor edge can be uncoated. The majority of the hand tool can be excluded from electrical current. The current can be provided through a wire. The current can be provided through an inset. The current can be provided through multiple layering of dielectric-conductive-dielectric coatings.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. A surgical tool comprising:
a first tip extending distally from a first handle; and
a second tip extending distally from a second handle;
wherein the surgical tool has a forceps configuration wherein the first and second tips operate as forceps;
wherein the surgical tool has a scissor configuration wherein the first and second tips operate as scissors;
wherein the surgical tool has a probe configuration wherein the first and second tips operate as a probe,
wherein the surgical tool is configured to allow selection between any configuration, wherein, once selected, the tool can operate only as forceps in the forceps configuration, only as scissors in the scissors configuration, and only as a probe in the probe configuration, wherein the first tip is configured to translate in a proximal-distal direction relative to the second tip and relative to the first handle and the second handle, and wherein the first tip is configured to translate distally or proximally while the first tip rotates about a longitudinal axis of the surgical tool in order to switch between the forceps configuration and the scissor configuration.

2. The surgical tool of claim 1, wherein the probe configuration is a configuration distinct from the forceps configuration and the scissor configuration.

3. The surgical tool of claim 1, wherein the first tip and the second tip are configured to be in contact in the probe configuration.

4. The surgical tool of claim 1, wherein the first tip comprises a first electrode.

5. The surgical tool of claim 1, wherein the first tip comprises a first electrode and the second tip comprises a second electrode.

6. The surgical tool of claim 1, wherein the first tip and the second tip operate as electrocautery bipolar forceps in the forceps configuration.

7. The surgical tool of claim 1, wherein the first tip and the second tip operate as an electrical monopolar probe in the probe configuration.

8. The surgical tool of claim 1, wherein one of the first tip and the second tip comprises a recess and the other of the first tip and the second tip comprises a protrusion, wherein the protrusion is configured to be received by the recess in the scissor configuration.

9. The surgical tool of claim 1, wherein at least one tip comprises a cross-section in the form of a droplet.

10. The surgical tool of claim 1, wherein at least one tip has a retractable blade.

11. The surgical tool of claim 1, wherein at least one tip has a foldable blade.

12. The surgical tool of claim 1, wherein the surgical tool comprises a plurality of apertures.

13. The surgical tool of claim 1, wherein the translation locks or releases a pin and a recess, wherein the pin and recess provide an axis upon which the first tip and the second tip pivot relative to each other in the scissor configuration.

14. A method of using a surgical tool comprising:
providing a tool having a first tip extending distally from a first handle and a second tip extending distally from a second handle, wherein the first and second tips operate as forceps in a forceps configuration;
wherein the first and second tips operate as a probe in a probe configuration;
wherein the first and second tips operate as scissors in a scissor configuration;
selecting between any configuration, wherein, once selected, the tool can operate only as forceps in the forceps configuration, only as scissors in the scissors configuration, and only as a probe in the probe configuration, wherein the first tip is configured to translate in a proximal-distal direction relative to the second tip and relative to the first handle and the second handle, and wherein the first tip is configured to translate distally or proximally while the first tip rotates about a longitudinal axis of the surgical tool in order to switch between the forceps configuration and the scissor configuration.

15. The method of claim 14, wherein when configured for use as a probe, the tool is configured for monopolar electrocautery, monopolar detection, or monopolar stimulation.

16. The method of claim 14, wherein when configured for use as a probe, the tool is configured for multipolar electrocautery, multipolar detection, or multipolar stimulation.

17. The method of claim 14, further comprising applying electrical energy to tissue with the first tip and the second tip.

18. The method of claim 14, further comprising applying electrical energy to tissue with only one of the first tip and the second tip.

* * * * *